(12) United States Patent
Baik et al.

(10) Patent No.: US 10,405,806 B2
(45) Date of Patent: Sep. 10, 2019

(54) APPARATUS FOR AND METHOD OF MEASURING BLOOD PRESSURE

(71) Applicant: SAMSUNG ELECTRONICS CO., LTD., Suwon-si (KR)

(72) Inventors: Chanwook Baik, Yongin-si (KR); Jisoo Kyoung, Seoul (KR); Maxim Vladimirovich Riabko, Dolgoprudniy (RU); Youngzoon Yoon, Hwaseong-si (KR); Alexey Dmitrievich Lantsov, Moscow Oblast (RU); Younggeun Roh, Seoul (KR); Jaesoong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 35 days.

(21) Appl. No.: 14/961,145

(22) Filed: Dec. 7, 2015

(65) Prior Publication Data

US 2016/0256116 A1 Sep. 8, 2016

(30) Foreign Application Priority Data

Mar. 6, 2015 (KR) .................. 10-2015-0031967

(51) Int. Cl.
*A61B 5/00* (2006.01)
*A61B 5/021* (2006.01)
(Continued)

(52) U.S. Cl.
CPC .......... *A61B 5/7278* (2013.01); *A61B 5/0059* (2013.01); *A61B 5/021* (2013.01);
(Continued)

(58) Field of Classification Search
CPC ............................ A61B 5/7278; A61B 5/7264
See application file for complete search history.

(56) References Cited

U.S. PATENT DOCUMENTS

| 4,987,900 A | 1/1991 | Eckerle et al. |
| 5,065,765 A | 11/1991 | Eckerle et al. |

(Continued)

FOREIGN PATENT DOCUMENTS

| CN | 104257371 A | 1/2015 |
| CN | 10-4970781 A | 10/2015 |

(Continued)

OTHER PUBLICATIONS

Enric Monte-Moreno, "Non-invasive estimate of blood glucose and blood pressure from a photoplethysmograph by means of machine learning techniques", Artificial Intelligence in Medicine, vol. 53, No. 2, Oct. 1, 2011, pp. 127-138.

(Continued)

*Primary Examiner* — Rochelle D Turchen
(74) *Attorney, Agent, or Firm* — Sughrue Mion, PLLC

(57) ABSTRACT

An apparatus for and a method of measuring blood pressure are provided. The apparatus includes a sensor configured to radiate light to a body part, and detect a light signal that is changed due to the body part. The apparatus further includes a signal processor configured to determine a bio signal based on the light signal; and a central processing unit configured to determine a blood pressure based on the bio signal and a blood pressure estimation algorithm.

16 Claims, 16 Drawing Sheets

(51) Int. Cl.
*A61B 5/024* (2006.01)
*A61B 5/1455* (2006.01)

(52) U.S. Cl.
CPC ............ *A61B 5/681* (2013.01); *A61B 5/6803* (2013.01); *A61B 5/6898* (2013.01); *A61B 5/7203* (2013.01); *A61B 5/7264* (2013.01); *A61B 5/742* (2013.01); *A61B 5/02416* (2013.01); *A61B 5/14552* (2013.01); *A61B 5/6824* (2013.01); *A61B 5/72* (2013.01); *A61B 2560/0475* (2013.01); *A61B 2562/0233* (2013.01)

(56) References Cited

U.S. PATENT DOCUMENTS

| | | | |
|---|---|---|---|
| 5,265,011 A | 11/1993 | O'Rourke | |
| 5,891,022 A | 4/1999 | Pologe | |
| 6,161,038 A | 12/2000 | Schookin et al. | |
| 6,475,153 B1 | 11/2002 | Khair et al. | |
| 6,571,193 B1 * | 5/2003 | Unuma | A43B 3/0005 340/853.2 |
| 7,123,363 B2 | 10/2006 | Puttappa et al. | |
| 7,231,243 B2 | 6/2007 | Tearney et al. | |
| 7,463,796 B2 | 12/2008 | Borgos et al. | |
| 7,641,614 B2 | 1/2010 | Asada et al. | |
| 7,657,135 B2 | 2/2010 | Borgos et al. | |
| 7,737,947 B2 | 6/2010 | Schroeder et al. | |
| 7,822,299 B2 | 10/2010 | Borgos et al. | |
| 7,925,056 B2 | 4/2011 | Presura et al. | |
| 8,032,200 B2 | 10/2011 | Tearney et al. | |
| 8,089,465 B2 | 1/2012 | Lutian | |
| 8,111,953 B2 | 2/2012 | Borgos et al. | |
| 8,217,897 B2 | 7/2012 | Lutian | |
| 8,277,384 B2 | 10/2012 | Fine | |
| 8,313,439 B2 | 11/2012 | McCombie et al. | |
| 8,343,062 B2 | 1/2013 | Fortin et al. | |
| 8,343,063 B2 | 1/2013 | Borgos | |
| 8,360,985 B2 | 1/2013 | Borgos | |
| 8,467,636 B2 | 6/2013 | Borgos et al. | |
| 8,496,595 B2 | 7/2013 | Jornod | |
| 8,808,188 B2 | 8/2014 | Banet et al. | |
| 8,868,149 B2 | 10/2014 | Eisen et al. | |
| 8,954,135 B2 | 2/2015 | Yuen et al. | |
| 9,097,516 B2 | 8/2015 | Hotta et al. | |
| 9,149,216 B2 | 10/2015 | Eisen et al. | |
| 9,277,868 B2 | 3/2016 | Borgos et al. | |
| 9,282,931 B2 | 3/2016 | Tearney et al. | |
| 9,326,711 B2 | 5/2016 | Kracker et al. | |
| 9,510,758 B2 | 12/2016 | Warger, II et al. | |
| 9,596,990 B2 | 3/2017 | Park et al. | |
| 9,603,524 B2 | 3/2017 | Park et al. | |
| 9,636,041 B2 | 5/2017 | Zalevsky et al. | |
| 9,668,672 B2 | 6/2017 | Zalevsky et al. | |
| 9,704,050 B2 | 7/2017 | Lee et al. | |
| 2002/0007125 A1 | 1/2002 | Hicket | |
| 2002/0095092 A1 | 7/2002 | Kondo et al. | |
| 2003/0013976 A1 | 1/2003 | Freund et al. | |
| 2004/0186387 A1 | 9/2004 | Kosuda et al. | |
| 2005/0228297 A1 | 10/2005 | Banet et al. | |
| 2007/0078308 A1 | 4/2007 | Daly | |
| 2007/0163353 A1 | 7/2007 | Lee et al. | |
| 2007/0265533 A1 | 11/2007 | Tran | |
| 2007/0276262 A1 | 11/2007 | Banet et al. | |
| 2007/0276632 A1 | 11/2007 | Banet at al. | |
| 2008/0071180 A1 | 3/2008 | Borgos | |
| 2008/0146952 A1 | 6/2008 | Presura et al. | |
| 2008/0181556 A1 | 7/2008 | Borgos et al. | |
| 2008/0183053 A1 | 7/2008 | Borgos et al. | |
| 2008/0228089 A1 | 9/2008 | Cho et al. | |
| 2009/0069698 A1 | 3/2009 | Bae et al. | |
| 2009/0073461 A1 | 3/2009 | Borgos et al. | |
| 2009/0209834 A1 | 8/2009 | Fine | |
| 2009/0209871 A1 | 8/2009 | Ueki et al. | |
| 2009/0326393 A1 | 12/2009 | Sethi et al. | |
| 2010/0022861 A1 | 1/2010 | Cinbis et al. | |
| 2010/0049059 A1 | 2/2010 | Ha et al. | |
| 2010/0145171 A1 | 6/2010 | Park et al. | |
| 2010/0160798 A1 | 6/2010 | Banet et al. | |
| 2010/0168589 A1 | 7/2010 | Banet et al. | |
| 2010/0210930 A1 | 8/2010 | Saylor | |
| 2010/0210956 A1 | 8/2010 | Im | |
| 2010/0324384 A1 | 12/2010 | Moon et al. | |
| 2011/0021931 A1 | 1/2011 | Borgos et al. | |
| 2011/0172505 A1 * | 7/2011 | Kim | A61B 5/02007 600/301 |
| 2011/0208066 A1 | 8/2011 | Gnadinger | |
| 2012/0025185 A1 | 2/2012 | Kasamatsu | |
| 2012/0108956 A1 | 5/2012 | Warger, II et al. | |
| 2012/0130215 A1 | 5/2012 | Fine et al. | |
| 2012/0130253 A1 | 5/2012 | Nadkarni et al. | |
| 2012/0130260 A1 | 5/2012 | Borgos et al. | |
| 2012/0136261 A1 | 5/2012 | Sethi et al. | |
| 2012/0143066 A1 | 6/2012 | Antonelli et al. | |
| 2012/0191001 A1 | 7/2012 | Segman | |
| 2013/0046192 A1 | 2/2013 | Lin et al. | |
| 2013/0131475 A1 | 5/2013 | Eisen et al. | |
| 2013/0144137 A1 | 6/2013 | Zalevsky et al. | |
| 2013/0190630 A1 | 7/2013 | Borgos | |
| 2013/0218025 A1 | 8/2013 | Tverskoy | |
| 2013/0245456 A1 | 9/2013 | Ferguson, Jr. et al. | |
| 2014/0012146 A1 | 1/2014 | Fukuda | |
| 2014/0066788 A1 | 3/2014 | Mukkamala et al. | |
| 2014/0066793 A1 | 3/2014 | Mukkamala et al. | |
| 2014/0081153 A1 | 3/2014 | Kuno | |
| 2014/0107493 A1 | 4/2014 | Yuen et al. | |
| 2014/0125491 A1 | 5/2014 | Park et al. | |
| 2014/0127996 A1 | 5/2014 | Park et al. | |
| 2014/0148658 A1 | 5/2014 | Zalevsky et al. | |
| 2014/0200423 A1 | 7/2014 | Eisen et al. | |
| 2014/0288435 A1 | 9/2014 | Richards et al. | |
| 2015/0105638 A1 | 4/2015 | Eisen et al. | |
| 2015/0117015 A1 | 4/2015 | Roh et al. | |
| 2015/0119725 A1 | 4/2015 | Martin et al. | |
| 2015/0126820 A1 | 5/2015 | Muhlsteff | |
| 2015/0323311 A1 | 11/2015 | Muijs et al. | |
| 2016/0058300 A1 | 3/2016 | Yoon et al. | |
| 2016/0066790 A1 | 3/2016 | Shcherbakov et al. | |
| 2016/0103985 A1 | 4/2016 | Shim et al. | |
| 2016/0106325 A1 | 4/2016 | Kang et al. | |
| 2016/0106327 A1 | 4/2016 | Yoon et al. | |
| 2016/0106333 A1 | 4/2016 | Kang et al. | |
| 2016/0113589 A1 | 4/2016 | Yoon | |
| 2016/0157736 A1 | 6/2016 | Huang et al. | |
| 2016/0192845 A1 | 7/2016 | Warger et al. | |
| 2016/0198961 A1 | 7/2016 | Homyk et al. | |
| 2016/0206251 A1 | 7/2016 | Kwon et al. | |
| 2016/0256116 A1 | 9/2016 | Baik et al. | |
| 2016/0256117 A1 | 9/2016 | Baik et al. | |
| 2016/0278645 A1 | 9/2016 | Yoon | |
| 2016/0278718 A1 | 9/2016 | Fujii et al. | |
| 2016/0287109 A1 | 10/2016 | Shim et al. | |
| 2016/0357154 A1 | 12/2016 | Shim et al. | |
| 2017/0017858 A1 | 1/2017 | Roh et al. | |
| 2017/0049340 A1 | 2/2017 | Cho et al. | |
| 2017/0055855 A1 | 3/2017 | Yoon | |
| 2017/0065184 A1 | 3/2017 | Barak | |
| 2017/0105679 A1 | 4/2017 | Gil | |
| 2017/0112395 A1 | 4/2017 | Kim et al. | |
| 2017/0135636 A1 | 5/2017 | Park et al. | |
| 2017/0150930 A1 | 6/2017 | Shikii et al. | |
| 2017/0172510 A1 | 6/2017 | Homyk et al. | |
| 2017/0209047 A1 | 7/2017 | Zalevsky et al. | |
| 2017/0245796 A1 | 8/2017 | Zalevsky et al. | |
| 2017/0251926 A1 | 9/2017 | Yoon et al. | |
| 2017/0319146 A1 | 11/2017 | Park et al. | |

FOREIGN PATENT DOCUMENTS

| | | |
|---|---|---|
| DE | 10 2010 014 761 A1 | 10/2011 |
| EP | 0755221 B1 | 10/2001 |
| EP | 1 204 370 B1 | 4/2008 |
| EP | 3072441 A1 | 9/2016 |
| JP | 11-155826 A | 6/1999 |

(56) References Cited

FOREIGN PATENT DOCUMENTS

| | | |
|---|---|---|
| JP | 2000-166885 A | 6/2000 |
| JP | 2003-532478 A | 11/2003 |
| JP | 3769524 B2 | 4/2006 |
| JP | 2008-295576 A | 12/2008 |
| JP | 4506849 B2 | 7/2010 |
| JP | 4614184 B2 | 1/2011 |
| JP | 4645259 B2 | 3/2011 |
| JP | 4848732 B2 | 12/2011 |
| JP | 2012-57962 A | 3/2012 |
| JP | 2012-161507 A | 8/2012 |
| JP | 2012-187300 A | 10/2012 |
| JP | 2012202776 A | 10/2012 |
| JP | 2013-509225 A | 3/2013 |
| JP | 2014-23031 A | 2/2014 |
| JP | 5528816 B2 | 6/2014 |
| JP | 2014240782 A | 12/2014 |
| JP | 2015502197 A | 1/2015 |
| KR | 10-0610813 B1 | 8/2006 |
| KR | 10-0650044 B1 | 11/2006 |
| KR | 10-2008-0073988 A | 8/2008 |
| KR | 10-2009-0052442 A | 5/2009 |
| KR | 10-2010-0060141 A | 6/2010 |
| KR | 10-2010-0065084 A | 6/2010 |
| KR | 10-1007354 B1 | 1/2011 |
| KR | 1020110025100 A | 3/2011 |
| KR | 10-1040598 B1 | 6/2011 |
| KR | 10-1058152 B1 | 8/2011 |
| KR | 10-1065615 B1 | 9/2011 |
| KR | 10-2012-0057813 A | 6/2012 |
| KR | 10-1310464 B1 | 9/2013 |
| KR | 10-2014-0024845 A | 3/2014 |
| KR | 10-1503604 B1 | 3/2015 |
| KR | 10-1560287 B1 | 10/2015 |
| KR | 10-1564066 B1 | 10/2015 |
| KR | 10-2016-0041553 A | 4/2016 |
| KR | 10-2016-0088127 A | 7/2016 |
| KR | 10-2016-0107007 A | 9/2016 |
| KR | 10-2016-0108081 A | 9/2016 |
| KR | 10-2017-0104361 A | 9/2017 |
| KR | 10-2017-0124943 A | 11/2017 |
| WO | 2015/129949 A1 | 9/2015 |

OTHER PUBLICATIONS

Communication dated Aug. 30, 2016 issued by the European Patent Office in counterpart European Patent Application No. 16158751.4.
Zhang et al., "A LabVIEW Based Measure System for Pulse Wave Transit Time"; Proceedings of the 5th International Conference on Information Technology and Application in Biomedicine, in conjunction with the 2nd International Symposium & Summer School on Biomedical and Health Engineering; May 30-31, 2008; 4 pgs. Total, pp. 477-480.
Yan et al., "Noninvasive Estimation of Blood Pressure Using Photophlethysmographic Signals in the Period Domain"; Proceedings of the 2005 IEEE Engineering in Medicine and Biology 27th Annual Conference; Sep. 1-4, 2005; pp. 3583-3584, 2 pgs. total.
Fortino et al., "PPG-based Methods for Non Invasive and Continuous Blood Pressure Measurement: an Overview and Development Issues in Body Sensor Networks"; IEEE; 2010; 4 pgs. total.
Kurylyak, et al., "A Neural Network-based Method for Continuous Blood Pressure Estimation from a PPG Signal"; Instrumentation and Measurement Technology Conference (I2MTC); May 6-9, 2013; 4pgs. Total, pp. 280-283.
Teng et al., "Continuous and Noninvasive Estimation of Arterial Blood Pressure Using a Photoplethysmographic Approach"; Proceedings of the 25th Annual International Conference of the IEEE EMBS; Sep. 17-21, 2003; 4 pgs. Total, pp. 3153-3156.
Young-Zoon Yoon.,"Study on cardiovascular system with blood pressure waveform and heart rate variability", A Dissertation Submitted to the Faculty of Seoul National University in Partial Fulfillment of the Requirements for the Degree of Doctor of Philosophy, School of Physics, Graduate School, Seoul National University, 2005, (210 Pages Total).
Chen et al., "Estimation of Central Aortic Pressure Waveform by Mathematical Transformation of Radial Tonometry Pressure; Validation of Generalized Transfer Function", 1997: 95, 1827-36, 12 pages total, American Heart Association.
O'Rourke et al., "Pulse wave analysis", Research Methods in Human Cardiovascular Pharmacology, 2001, Clinical Pharmacology, Blackwell Science Ltd Br J Clin Pharmacol: 51, pp. 507-522, 16 pages total.
Aymen A. Awad et al., "How Does the Plethysmogram Derived from the Pulse Oximeter Relate to Arterial Blood Pressure in Coronary Artery Bypass Graft Patients?"; Anesth Analg, 93; 2001; pp. 1466-1471; 6 pgs. total.
Satomi Suzuki, et al., "Cuffless and Non-invasive Systolic Blood Pressure Estimation for Aged Class by Using a Photoplethysmograph"; 30th Annual International IEEE EMBS Conference; Aug. 20-24, 2008; pp. 1327-1330; 4 pgs. total.
Arata Suzuki et al., "Feature Selection Method for Estimating Systolic Blood Pressure Using the Taguchi Method"; IEEE Transactions on Industrial Informatics; vol. 10; No. 2; May 2014; pp. 1077-1085; 9 pgs. total.
Y. Kurylyak et al., "Photoplethysmogram-based Blood Pressure Evaluation using Kalman Filtering and Neural Networks"; Medical Measurements and Applications Proceedings (MeMeA), 2013 IEEE International Symposium; May 4, 2013; 5 pgs. total.
Yevgeny Beiderman et al., "Remote estimation of blood pulse pressure via temporal tracking of reflected secondary speckles pattern"; Journal of Biomedical Optics; vol. 15; No. 6; Nov./Dec. 2010; pp. 061707-1-061707-7; 7 pgs. total.
Yu.N. Kul'Chin et al., "Correlation method for processing speckles of signals from single-fibre multimode interferometers by using charge-coupled devices"; Optical Fibres and Waveguides; Quantum Electronics; vol. 36; No. 4; 2006; pp. 339-342; 5 pgs. total.
Ramakrishna Mukkamala et al., "Towards Ubiquitous Blood Pressure Monitoring via Pulse Transit Time: Theory and Practice", IEEE Trans Biomed Eng. Aug. 2015 ; 62(8), pp. 1879-1901, 48 pages total.
Qing Liu et al., "Attenuation of Systolic Blood Pressure and Pulse Transit Time Hysteresis During Exercise and Recovery in Cardiovascular Patients", IEEE Transactions on Biomedical Engineering, vol. 61, No. 2, Feb. 2014, pp. 346-352.
R. A. Payne et al., " Pulse transit time measured from the ECG: an unreliable marker of beat-to-beat blood pressure", J Appl Physiol, the American Physiological Society 100, 2006, pp. 136-141.
Communication from United States Patent and Trademark Office dated Jun. 28, 2017, in U.S. Appl. No. 14/844,437.
Communication from United States Patent and Trademark Office dated Mar. 20, 2017, in U.S. Appl. No. 14/818,420.
Communication from United States Patent and Trademark Office dated Jun. 16, 2017, in U.S. Appl. No. 14/818,420.
Communication from United States Patent and Trademark Office dated Apr. 17, 2017, in U.S. Appl. No. 15/068,760.
Jianjun Qiu et al; "Spatiotemporal laser speckle contrast analysis for blood flow imaging with maximized speckle contrast"; Journal of Biomedical Optics; vol. 15; No. 1; Jan./Feb. 2010; pp. 016003-1-016003-5; 5pgs. total.
Dr. S. Shah et al; "Optoelectronic blood pressure estimation: A novel principle for blood pressure measurement"; Tarilian Laser Technologies; (http://www.tarilian-lasertechnologies.com/press/tlt-at-esh2012.php); 2012; 4 pgs. total.
"Tarilian Laser Technologies achieves greatest technological advance in blood pressure measurement for 130 years"; (http://www.tarilian-lasertechnologies.com/press/pr111201.php); Tarilian Laser Technologies; Dec. 7, 2011; 6 pgs. total.
Kurylyak et al., "A Neural Network-based Method for Continuous Blood Pressure Estimation from a PPG Signal", Conference (I2MTC), 2013 IEEE International, (4 pages total).
Communication dated Dec. 14, 2017 issued by the European Patent Office in counterpart Application No. 17172684.7.
Anonymous, "Central Venous Pressure Waveforms", Section 3: Anesthesia Management, Part B: Monitoring, Chapter 30: Cardiovascular Monitoring, 1979, http://web.squ.edu.om/med-Lib/MED_CD/E_CDs/anesthesia/site/content/v03/030275r00.HTM; 4 pages total.

(56) References Cited

OTHER PUBLICATIONS

Notice of Allowance dated Mar. 4, 2019 issued by the USPTO in counterpart U.S. Appl. No. 14/818,420.
Final Office Action dated Mar. 7, 2019 issued by the USPTO in counterpart U.S. Appl. No. 14/833,221.
Notice of Allowance dated Mar. 18, 2019 issued by the USPTO in counterpart U.S. Appl. No. 15/068,760.
Non-Final Office Action dated Mar. 22, 2019 issued by the USPTO in counterpart U.S. Appl. No. 14/862,288.
U.S. Final OA dated Sep. 26, 2017 issued by the USPTO in counterpart U.S. Appl. No. 15/068,760.
U.S. Non-Final Office Action dated Nov. 1, 2017 issued by the USPTO in counterpart U.S. Appl. No. 14/862,288.
U.S. Non-Final Office Action dated Dec. 22, 2017 issued by the USPTO in counterpart U.S. Appl. No. 14/818,420.
U.S. Non-Final Office Action dated Jan. 30, 2018 by the United States Patent and Trademark Office in U.S. Appl. No. 15/068,760.
Restriction Requirement dated Mar. 8, 2018 by the USPTO in counterpart U.S. Appl. No. 14/833,221.
U.S. Final Office Action dated May 23, 2018 by United States Patent and Trademark Office, in U.S. Appl. No. 14/862,288.
U.S. Final Office Action dated Jul. 16, 2018 by the United States Patent and Trademark Office in U.S. Appl. No. 15/068,760.
U.S. Non-Final Office Action dated Jul. 26, 2018 by the United States Patent and Trademark Office in U.S. Appl. No. 14/833,221.
U.S. Advisory Action dated Aug. 2, 2018 by the United States Patent and Trademark Office in U.S. Appl. No. 14/862,288.
U.S. Final Office Action dated Aug. 6, 2018 by the United States Patent and Trademark Office in U.S. Appl. No. 14/818,420.
Restriction Requirement dated Sep. 6, 2018 issued by the USPTO in counterpart U.S. Appl. No. 14/884,019.
Notice of Allowance dated Oct. 24, 2018, issued by United States Patent and Trademark Office in U.S. Appl. No. 15/068,760.
Notice of Allowance dated Nov. 15, 2018, issued by United States Patent and Trademark Office in U.S. Appl. No. 14/818,420.
U.S. Non-Final Office dated Dec. 14, 2018 issued by the USPTO in counterpart U.S. Appl. No. 14/884,019.
Restriction Requirement dated Jan. 14, 2019 issued by the USPTO in counterpart U.S. Appl. No. 15/654,422.
U.S. Non-Final OA dated Aug. 24, 2017 issued by the USPTO in counterpart U.S. Appl. No. 14/844,437.
U.S. Final OA dated Mar. 8, 2018 issued by the USPTO in counterpart U.S. Appl. No. 14/844,437.
U.S. Non-Final OA dated Jun. 15, 2018 issued by the USPTO in counterpart U.S. Appl. No. 14/844,437.
Notice of Allowance dated Nov. 7, 2018 issued by the USPTO in counterpart U.S. Appl. No. 14/844,437.
Advisory Action dated Dec. 19, 2017 issued by the USPTO in counterpart U.S. Appl. No. 15/068,760.
Non-Final Office Action dated Apr. 26, 2019 issued by the USPTO in counterpart U.S. Appl. No. 15/654,422.
Communication dated Jun. 20, 2019, issued by the United States Patent and Trademark Office in counterpart U.S. Appl. No. 14/884,019.

* cited by examiner

1 CYCLE EXTRACT

APPARATUS FOR AND METHOD OF MEASURING BLOOD PRESSURE

CROSS-REFERENCE TO RELATED APPLICATION

This application claims priority from Korean Patent Application No. 10-2015-0031967, filed on Mar. 6, 2015, in the Korean Intellectual Property Office, the disclosure of which is incorporated herein by reference in its entirety.

BACKGROUND

1. Field

Apparatuses and methods consistent with exemplary embodiments relate to apparatuses for and methods of measuring blood pressure.

2. Description of the Related Art

Blood pressure is used as a measure of health. Sphygmomanometers are devices for measuring blood pressure and are commonly used in medical institutions and at home. In the case of a cuff-type sphygmomanometer, a systolic blood pressure and a diastolic blood pressure are measured by placing a cuff around a body part through which arterial blood flows, inflating the cuff until the artery is occluded, and then slowly releasing the pressure in the cuff. However, the cuff-type sphygmomanometer causes inconvenience to a user due to the applied pressure, and is inconvenient to carry to continuously monitor a change in the blood pressure of a person in real time for a long time. Accordingly, much research on cuffless sphygmomanometers for measuring blood pressure has been made.

SUMMARY

Exemplary embodiments address at least the above problems and/or disadvantages and other disadvantages not described above. Also, the exemplary embodiments are not required to overcome the disadvantages described above, and may not overcome any of the problems described above.

Exemplary embodiments provide apparatuses for and methods of measuring blood pressure based on a light signal via a cuffless structure. The blood pressure may be continuously monitored for a long time.

According to an aspect of an exemplary embodiment, there is provided an apparatus configured to measure blood pressure, the apparatus including a sensor configured to radiate light to a body part, and detect a light signal that is changed due to the body part. The apparatus further includes a signal processor configured to determine a bio signal based on the light signal, and a central processing unit configured to determine a blood pressure based on the bio signal and a blood pressure estimation algorithm.

The signal processor may be further configured to extract a cycle of the light signal, and sample data from the cycle of the light signal at equidistant time intervals or based on a user input.

The signal processor may be further configured to compare power spectrums within a frequency range of bio signals that are determined based on channels, and select a channel having a maximum power spectrum from the channels.

The signal processor may be further configured to, in response to the signal processor selecting the channel having the maximum power spectrum or using a single channel, select a part of a bio signal that corresponds to the selected channel or the single channel, in which a power spectrum value within the frequency range is greater than a value, as a valid part of the bio signal.

The apparatus may further include a display configured to display the blood pressure.

The apparatus may further include a memory configured to store the blood pressure estimation algorithm.

The sensor may include a light emitter configured to radiate the light to the body part, and a light receiver configured to detect the light signal that is changed due to the body part. The light receiver may include a photodiode or an image sensor, and the light emitter may include a laser diode or a light emitting diode.

The sensor may include a light emitter configured to radiate the light to the body part, and a light receiver configured to detect the light signal that is changed due to the body part, the light emitter may include a laser diode, and the central processing unit may be further configured to determine the blood pressure based on the bio signal in response to the sensor being spaced apart from a skin of an examinee.

The bio signal may be periodically obtained at predetermined time intervals.

The central processing unit may be further configured to determine the blood pressure based on the bio signal and one among a linear regression analysis algorithm, a multiple regression analysis algorithm, and a non-linear regression analysis algorithm.

The central processing unit may be further configured to determine the blood pressure based on the bio signal and one among an artificial neural network algorithm, a k-nearest neighbor algorithm, a Bayesian network algorithm, a support vector machine algorithm, and a recurrent neural network algorithm.

The central processing unit may be further configured to correct the blood pressure based on a blood pressure that is determined by another device.

The apparatus may further include a body information interface configured to receive body information of at least one among an age, a gender, a weight, and a height of an examinee, and the central processing unit may be further configured to determine the blood pressure based on the bio signal and the body information.

The apparatus may be portable, and may be implemented in one among a wrist watch, a mobile smart phone, a tablet computer, an earphone, a headset, and glasses.

The apparatus may be implemented in a wrist watch, and the sensor may be positioned on a back of a main body or a strap of the wrist watch.

According to an aspect of another exemplary embodiment, there is provided a method of measuring blood pressure, the method including radiating light to a body part, detecting a light signal that is changed due to the body part, and determining a bio signal based on the light signal. The method further includes correcting the bio signal, extracting feature points from the corrected bio signal, and combining a matrix of a blood pressure estimation algorithm with the feature points to determine a blood pressure.

The extracting may include determining a maximum point of the corrected bio signal and a minimum point adjacent to the maximum point, and extracting the feature points from the corrected bio signal at equidistant time intervals or based on a user input.

The matrix of the blood pressure estimation algorithm may be determined by learning the blood pressure estimation algorithm such that the blood pressure that is determined by inputting the feature points in the blood pressure estimation algorithm is closer to an actual blood pressure.

The blood pressure estimation algorithm may be one among an artificial neural network algorithm, a k-nearest neighbor algorithm, a Bayesian network algorithm, a support vector machine algorithm, and a recurrent neural network algorithm.

The correcting may include correcting a baseline of a sequence of the bio signal, and removing high frequency noise from the corrected sequence.

BRIEF DESCRIPTION OF THE DRAWINGS

The above and/or other aspects will be more apparent by describing exemplary embodiments with reference to the accompanying drawings in which.

DETAILED DESCRIPTION OF THE EXEMPLARY EMBODIMENTS

Figure 1:
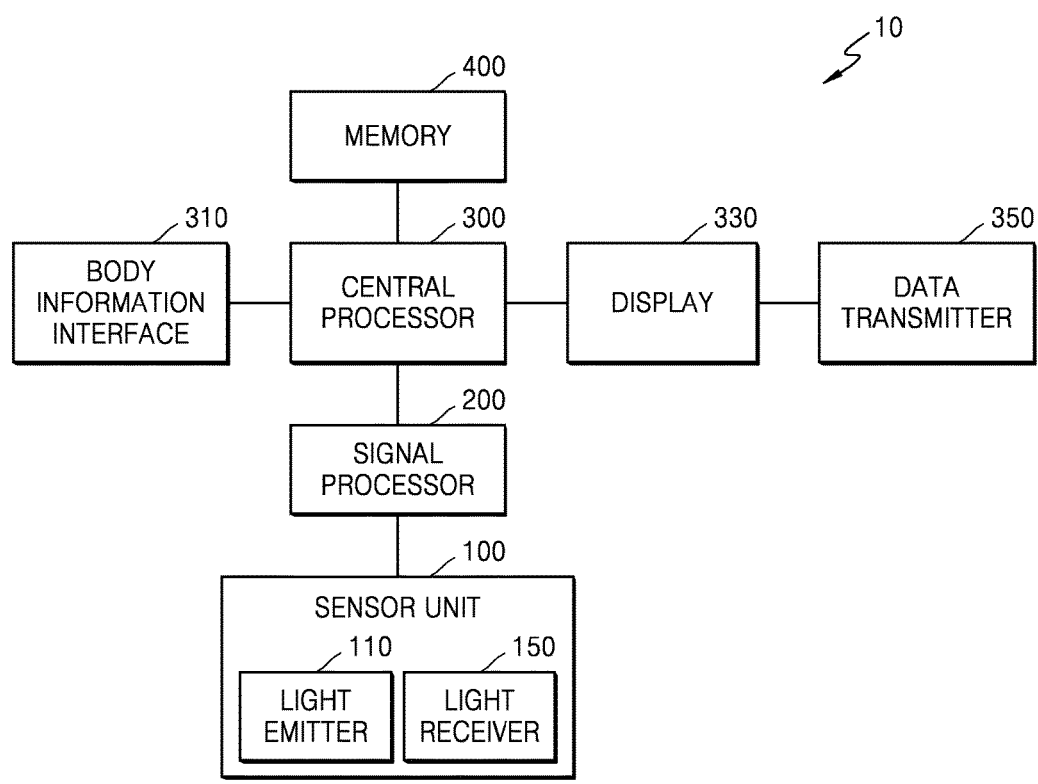
FIG. 1 is a block diagram of a blood pressure measuring apparatus according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the description with unnecessary detail.

It will be understood that although the terms "first," "second," etc. may be used herein to describe various elements, these elements should not be limited by these terms. These elements are only used to distinguish one element from another.

In addition, the terms such as "unit," "-er (-or)," and "module" described in the specification refer to an element for performing at least one function or operation, and may be implemented in hardware, software, or the combination of hardware and software.

FIG. 1 is a block diagram of a blood pressure measuring apparatus 10 according to an exemplary embodiment.

Referring to FIG. 1, the blood pressure measuring apparatus 10 includes a sensor 100, a signal processor 200 that obtains a bio signal from a signal detected from the sensor 100, a memory 400 that stores a blood pressure estimation algorithm, and a central processing unit 300 that calculates blood pressure based on the obtained bio signal by using the blood pressure estimation algorithm. The blood pressure measuring apparatus 10 further includes a display 330 that displays the calculated blood pressure, a body information interface 310 that inputs body information to increase the accuracy of calculating the blood pressure, and a data transmitter 350 that transmits information about the calculated blood pressure to another device.

The sensor 100 radiates light towards an examined body part, and detects a signal change in the light that is caused by the examined body part. The sensor 100 includes a light emitter 110 and a light receiver 150. The light emitter 110 may include at least one light emitting device, and the light receiver 150 may include at least one light receiving device.

The light emitting device may be a light emitting diode (LED) or a laser diode (LD). The light receiving device may include a photodiode or an image sensor, for example, a CMOS image sensor (CIS). A phototransistor (PTr) may be used as the light receiving device. The light receiving device may be configured to sense a signal change according to a blood stream change of light scattered or reflected from the examined body, i.e., skin of an examinee or a blood vessel.

FIGS. 2 through 5 are layouts of a light emitting device 111 and a light receiving device 151 of the sensor 100 according to exemplary embodiments. A case where the light emitting device 111 and the light receiving device 151 are disposed on a same substrate 101 will now be described with reference to FIGS. 2 through 5 as examples.

Figure 2:
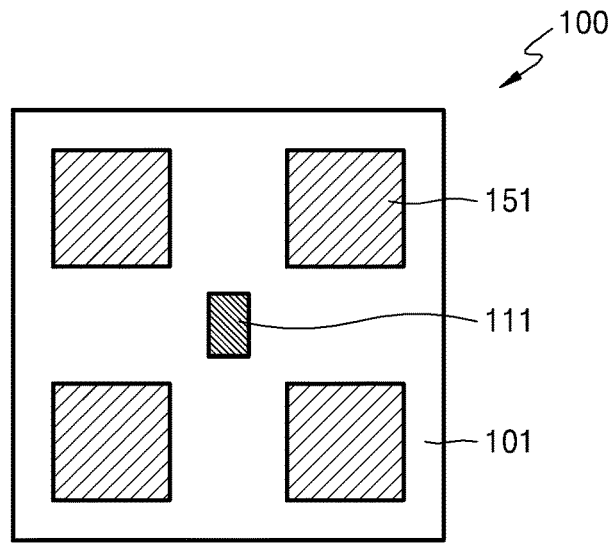
FIGS. 2 through 5 are layouts of a light emitting device and a light receiving device of a sensor according to exemplary embodiments.
Figure 3:
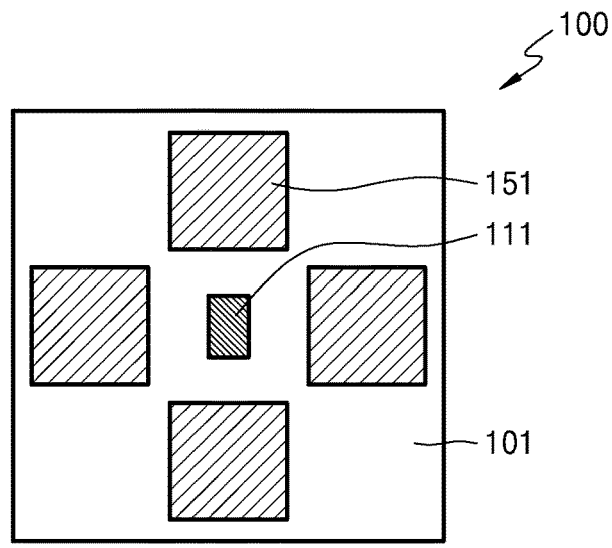
Figure 4:
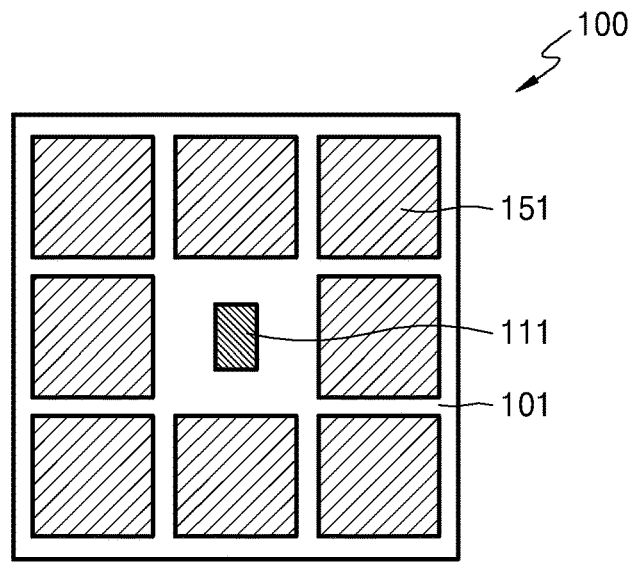

Referring to FIGS. 2 through 4, the light emitting device 111 is disposed in a center of the sensor 100, and the light receiver 150 includes a plurality of light emitting devices 151 surrounding the light emitting device 111.

Figure 5:
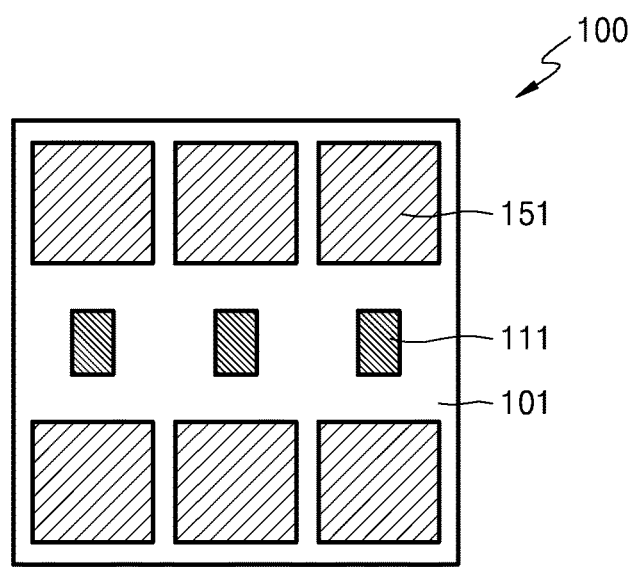

In another example, referring to FIG. 5, the sensor 100 has a structure in which an array of a plurality of light emitting devices 111 and an array of the plurality of light receiving devices 151 are disposed in parallel. In this regard, the array of the plurality of light emitting devices 111 is disposed in the center of the sensor 100, and the array of the plurality of light receiving devices 151 is disposed along at least one side of the array of the plurality of light emitting devices 111.

FIG. 5 illustrates an example in which arrays of the plurality of light receiving devices 151 are respectively disposed along two sides of the array of the plurality of light emitting devices 111.

As shown in FIGS. 2 through 5, when the light emitting device 111 is disposed in the center of the sensor 100 and the light emitting devices 151 are disposed around the light emitting device 111, a light receiving amount of light scattered or reflected from an examined body part, for example, a skin surface of an examinee or a blood vessel, may increase. The light emitting device 111 and the plurality of light receiving devices 151 that configure the sensor 100 are not limited to those shown in FIGS. 2 through 5, and may have various layouts. For example, at least one of the light emitting devices 151 may be disposed in the center of the sensor 100, and one or more light emitting devices 111 may be disposed around the at least one of the light emitting devices 151.

Meanwhile, when a laser diode is used as the light emitting device 111 of the light emitter 110, due to the directional property of a laser beam emitted by the laser diode, a signal may be measured although the sensor 100 is spaced apart from the skin surface of the examinee. Thus, when a laser diode is used as the light emitting device 111, and the blood pressure measuring apparatus 10 is implemented as a wristwatch-type device, a device having a structure in which the sensor 100 is placed on the back side of a main body and the signal is measured from the wrist or the back of a hand, may be implemented. The wristwatch-type device includes a main body and a strip being worn on the wrist. An adherence of the strip to the wrist may be better than an adherence of the main body to the wrist. The main body of the wristwatch-type device may be spaced apart from a skin surface of the wrist. When a laser diode is provided as the light emitting device 111 and the sensor 100 is placed on the back side of the main body, the blood pressure may be measured irrespective of a state of wearing the device, i.e., a contact state or a non-contact state with respect to the wrist.

In this regard, when an LED is used as the light emitting device 111, according to the spread characteristics of light emitted by the LED, an operation of measuring the blood pressure may be performed by more tightly closing the sensor 100 to the skin of the examinee than in the case when a laser diode is used as the light emitting device 111. However, when an LED is used as the light emitting device 111, the blood pressure may be measured even when the sensor 100 and the skin surface of the examinee are spaced apart from each other within a range in which a signal is detectable.

Referring again to FIG. 1, the signal processor 200 obtains a bio signal from the signal detected from the sensor 100, and removes a signal change component of light due to external illumination or an external environment. The signal processor 200 analyzes an intensity change of the signal detected from the sensor 100 on a time basis. The bio signal may be obtained by analyzing a fluctuation of a light signal corresponding to a capacity change of a blood vessel (for example, a blood vessel on a finger, an upper side of a wrist or a radial artery on a lower side of the wrist) of the examined body. In this regard, the obtained bio signal may be a photoplethysmogram (PPG) signal converted based on a correlation of the analyzed fluctuation of the light signal and the capacity change. A digital to analogue converter (DAC) or an ADC may be applied as the signal processor 200.

The signal processor 200 may include a waveform extracting unit that, for example, extracts in real time one cycle of a waveform of a signal that is input, and a data extracting unit that samples data at equivalent time intervals or by using a user-defined method from one cycle of the waveform. The signal processor 200 may further include a waveform selecting unit.

The signal processor 200 may be configured to obtain the bio signal from each of a plurality of channels. The signal processor 200 may compare power spectrums within a previously set frequency range (for example, about 0.66 Hz~about 3 Hz) with respect to a waveform of a bio signal obtained from each of the plurality of channels, and select a channel having a largest power spectrum. As another example, the signal processor 200 may be configured to use a single channel. According to use of the selected channel or the single channel, the waveform selecting unit may select a waveform part of the bio signal in which a power spectrum value within a predetermined frequency range is greater than a previously set value as a valid waveform part.

The memory 400 may store a blood pressure estimation algorithm. The memory 400 may store a program for processing and controlling the signal processor 200 and the central processing unit 300, and may also store data that is input/output. That is, the memory 400 may store measurement results of the sensor 100 or a bio signal obtained by the signal processor 200 via signal processing. The memory 400 may be configured to store a bio signal obtained in real time in a buffer memory, and may be configured to call the blood pressure estimation algorithm and calculate a blood pressure.

The memory 400 may include at last one type of storage medium among, for example, a flash memory type, a hard disk type, a multimedia card micro type, card type memory (for example, SD or XD memory, etc.), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disk, and an optical disk.

The central processing unit 300 controls an operation of the sensor 100, and calculates blood pressure from the measured signal by using the blood pressure estimation algorithm. That is, the central processing unit 300 calculates blood pressure from the bio signal obtained by processing the signal measured by the sensor 100 in the signal processor 200 by using the blood pressure estimation algorithm. The central processing unit 300 may control the memory 400, the display 330, the signal processor 200, the body information interface 310, etc.

The central processing unit 300 may analyze various feature points of the bio single by analyzing a waveform characteristic of the bio signal, for example, a PPG pulse wave signal. The central processing unit 300 may also estimate blood pressure values by combining data of the analyzed feature points and a matrix of the blood pressure estimation algorithm. In this regard, the blood pressure values estimated by the central processing unit 300 may include a systolic blood pressure (SBP), a diastolic blood pressure (DBP), a heart rate (HR), etc.

The blood pressure values calculated by the central processing unit 300 may be displayed on the display 330. The display 330 may be configured to display the SBP and the DBP, and may be configured to display the HR.

The body information interface 310 may be configured to input at least one piece of body information among an age, a gender, a weight, and a height of the examinee to increase accuracy of calculating the blood pressure. The central processing unit 300 may operate to estimate the blood pressure for each of the body information input through the body information interface 310. In this regard, when the blood pressure estimation algorithm is configured to collect data of a randomly extracted population, the blood pressure measuring apparatus 10 may be configured by omitting the body information interface 310.

The data transmitter 350 transmits a result analyzed by the central processing unit 300 to an external different device. The blood pressure values calculated and estimated by the central processing unit 300 may be output through the display 330. The data transmitter 350 may transmit the blood pressure values and a heat rate value to an external device such as a smart phone or a computer by using, for example, a communication protocol such as Bluetooth. The data transmitter 350 may be used to connect devices or connect a device to a clinic to allow the clinic to provide various services.

In this regard, the external device may be not only the smart phone or the computer but also, for example, medical equipment that uses information of an analyzed blood pressure, a printer that prints a resultant, or a display apparatus that displays an analysis result. In addition, the external device may be various devices such as a tablet PC, a personal digital assistant (PDA), a laptop, PC, and another mobile or non-mobile computing apparatus.

The data transmitter 350 may be connected to the external device by wire or wirelessly. For example, the data transmitter 350 may be configured to communicate with the external device by using various communication methods such as Bluetooth communication, Bluetooth Low Energy (BLE) communication, Near Field Communication, WLAN (WiFi) communication, Zigbee communication, infrared Data Association (IrDA) communication, WFD (Wi-Fi Direct) communication, ultra wideband (UWB) communication, Ant+ communication, etc.

Meanwhile, the blood pressure measuring apparatus 10 may further include a user interface. The user interface may be for an interface of the user and/or the external device, and may include an input unit and an output unit. In this regard, although the user is an individual of which blood pressure is to be measured, i.e., an examinee, the user may also be a person, such as a medical expert, who may use the blood pressure measuring apparatus 10. Thus, the term "user" may have wider range than that of the term "examinee." The user interface may be used to input information for operating the blood pressure measuring apparatus 10, and output an analyzed result. The user interface may include, for example, a button, a connector, a keypad, a display, etc., and may further include an element such as a sound output unit or a vibration motor.

The blood pressure measuring apparatus 10 may be configured to be mobile as a wearable device, a mobile phone, for example, a mobile smart phone, or a tablet device. That is, the blood pressure measuring apparatus 10 may be mounted in a wearable device, a mobile phone, for example, a mobile smart phone, or a tablet device. The blood pressure measuring apparatus 10 may be configured as a device to be put on a finger to measure the blood pressure, for example, a device of a finger tongs type.

For example, the blood pressure measuring apparatus 10 may be implemented in a device that may be worn on the examinee, i.e., in the wearable device. In this regard, the wearable device may be implemented in a wrist watch type, a bracelet type, and a wrist band type, and may be additionally implemented in various types such as a ring type, a glasses type, an earphone type, a headset type, or a hair band type. Some elements of the blood pressure measuring apparatus 10, for example, the sensor 100 and the signal processor 200, may be implemented in a type that may be worn by the examinee.

The blood pressure measuring apparatus 10 may be used as a device for estimating the blood pressure of the examinee and measuring a heart rate of the examinee by being applied instead of a sensor of a wrist watch type wearable device that measures the heart rate only, for example, by using the back of the main body (corresponding to a watch in a wrist watch). The blood pressure measuring apparatus 10 may be used as the device for estimating the blood pressure of the examinee and measuring the heart rate of the examinee by being applied to a smart phone that uses a light emitting device and a CIS.

Figure 6:
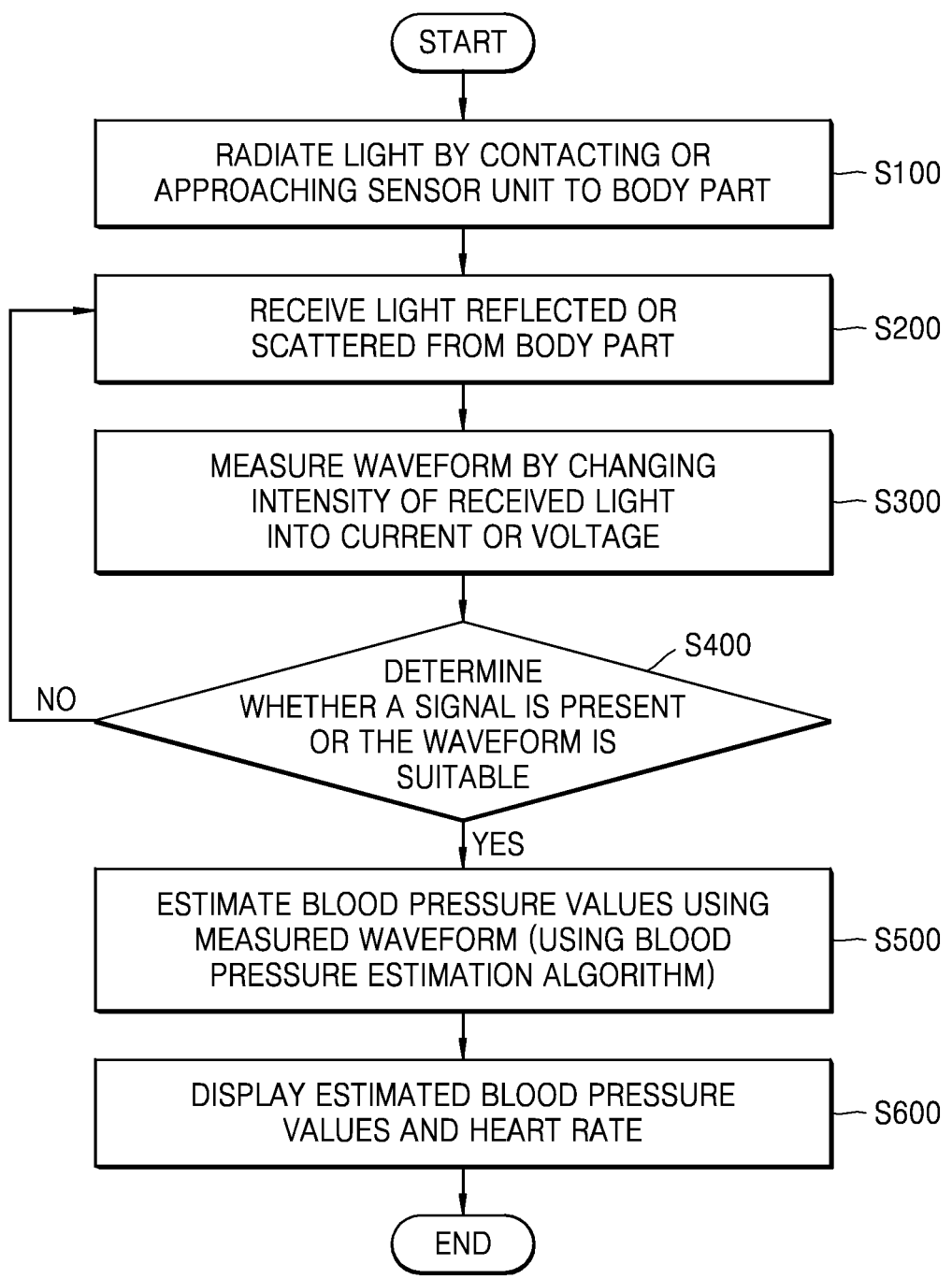
FIG. 6 is a flowchart of an operation of a blood pressure measuring apparatus according to an exemplary embodiment.

FIG. 6 is a flowchart of an operation of the blood pressure measuring apparatus 10 according to an exemplary embodiment.

Referring to FIG. 6, the light emitter 110 of the sensor 100 radiates light to skin by contacting or approaching a body part of an examinee, for example, a finger, a wrist, etc. (operation S100). In this regard, the light receiver 150 receives light reflected or scattered from the body part (operation S200), and the signal processor 200 measures a waveform by changing an intensity of the received light into a current or voltage (operation S300).

The signal processor 200 or the central processing unit 300 determines whether a signal of the measured waveform is present or the waveform is suitable (operation S400). If the waveform is a waveform including a heart rate, operation S500 is performed. If not, operation S200 of receiving the reflected or scattered light is again performed.

The central processing unit 300 estimates blood pressure values using the measured waveform and a blood pressure estimation algorithm (operation S500). The display 330 displays the estimated blood pressure values and the heart rate (operation S600). In the operation of estimating the blood pressure values, a blood pressure value that is measured by another device may be input in the blood pressure estimation algorithm. In this case, the blood pressure estimation algorithm may correct the blood pressure values by using the blood pressure value that is measured by the other device.

The blood pressure measuring apparatus 10 according to the exemplary embodiment described above may read a change in a blood stream in a finger or an upper or lower side (a radial artery) of a wrist, as an intensity change in light, may estimate maximum and minimum points of the blood pressure, i.e., a SBP and a DBP, by applying the blood pressure estimation algorithm, and may also estimate an HR.

Figure 7:
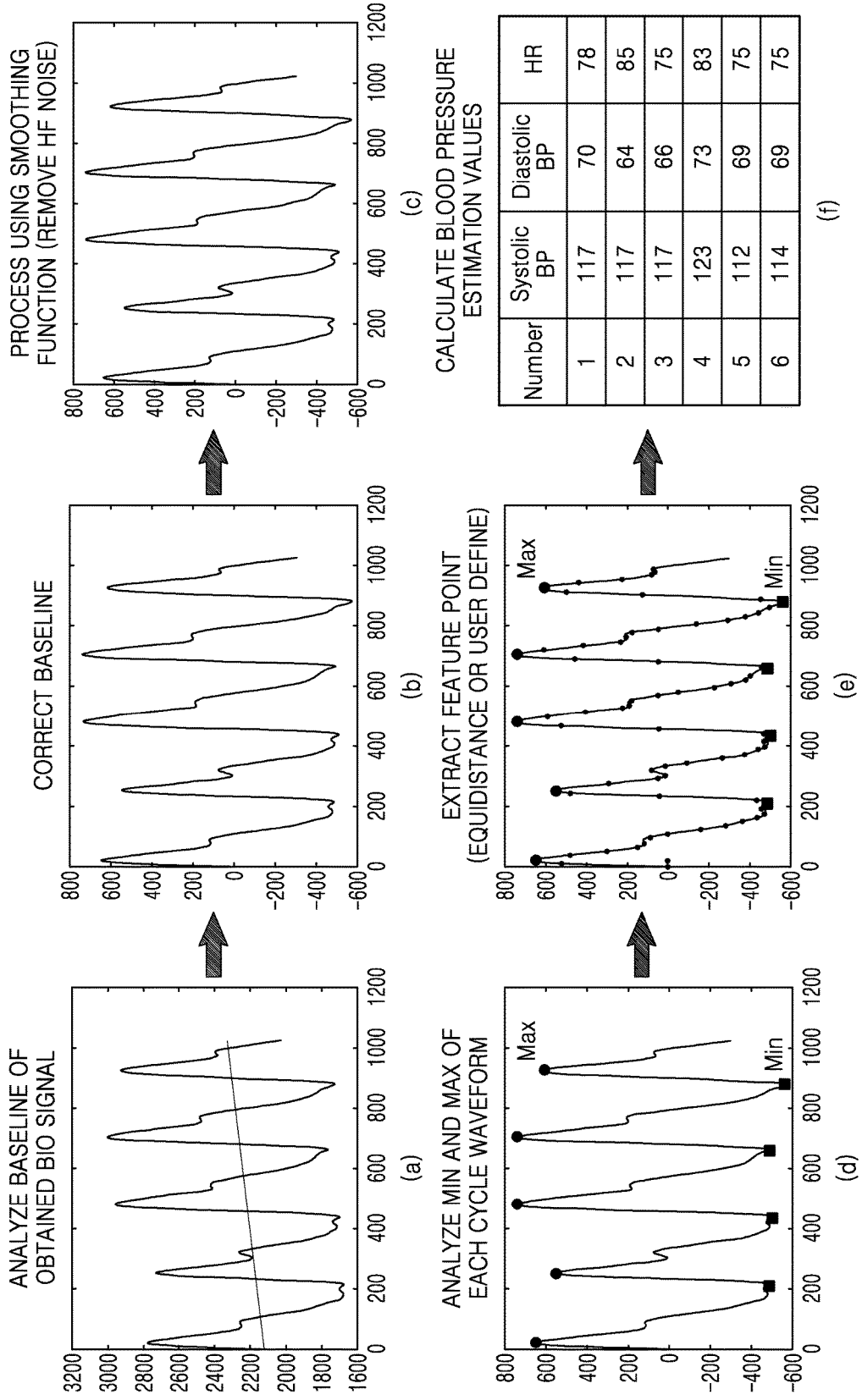
FIG. 7 is a diagram illustrating a process of estimating blood pressure via a blood pressure estimation algorithm according to an exemplary embodiment.

FIG. 7 is a diagram illustrating a process of estimating blood pressure via a blood pressure estimation algorithm according to an exemplary embodiment.

Referring to FIG. 7(*a*), a bio signal is obtained by radiating light to an examined body and detecting a signal change of light by the examined body. In this regard, a baseline with respect to the obtained bio signal is analyzed. The graph of FIG. 7(*a*) shows an example of measuring the bio signal for 4 seconds. The bio signal may be obtained a plurality of number of times at a time distance, for example, a predetermined time distance, for processing data. As shown in the graph of the bio signal of FIG. 7(*a*), the baseline may not be constant. FIG. 7(*a*) shows an example of drawing a primary function in which the baseline increases over time. The baseline may be in a secondary function, a tertiary function, or a function having a plurality of inflection points. In this regard, the baseline may be a line connecting, for example, intermediate points of a maximum point and a minimum point, of each cycle waveform of the bio signal.

When the baseline is drawn in the primary, secondary, or tertiary function by analyzing the baseline described above, a bio signal may be obtained as shown in FIG. 7(b) by correcting the baseline.

Next, referring to FIG. 7(c), when a bio signal includes high frequency HF noise, the high frequency HF noise may be removed by processing the bio signal using, for example, a smoothing function or filter. In this regard, when the bio signal does not include the high frequency HF noise, high frequency HF noise removing processing, such as processing using the smoothing function or the filter, may be omitted.

Next, a maximum point Max and a minimum point Min of each cycle waveform of the bio signal from which the high frequency HF noise is removed are analyzed as shown in FIG. 7(d), and feature points are extracted as shown in FIG. 7(e). The feature points of each cycle waveform may be extracted at equivalent or equidistant time intervals or may be extracted by determining a point from which the feature points are to be extracted by using a user-defined method.

When data of the extracted feature points is combined with a blood pressure estimation algorithm, as shown in FIG. 7(f), a blood pressure estimation value calculation results may be obtained. The blood pressure estimation value calculation result of FIG. 7(f) is obtained by using a bio signal obtained for 4 seconds for each calculation.

As shown in the blood pressure estimation value calculation result of FIG. 7(f), a SBP and a DBP may be estimated and a HR estimation value may be obtained through the process described above.

The blood pressure measuring apparatus 10 according to the exemplary embodiment may estimate a blood pressure, and measure a HR, by being applied to various existing devices that only measure the HR using light.

Figure 8:
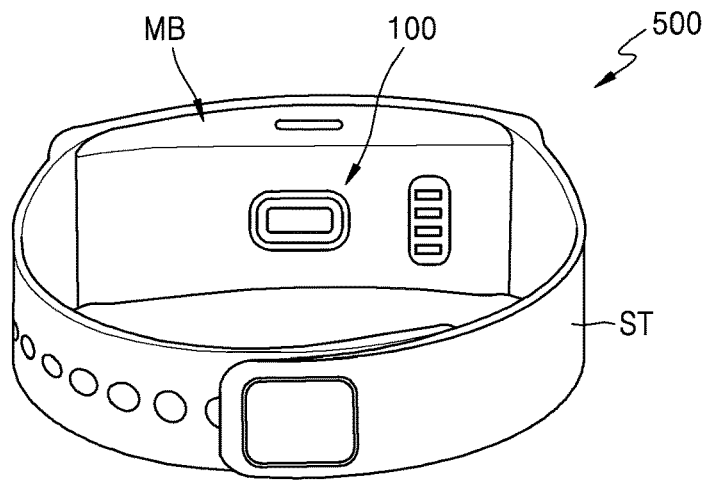
FIGS. 8 through 10 are perspective views of portable devices, each including a blood pressure measuring apparatus according to exemplary embodiments.
Figure 9:
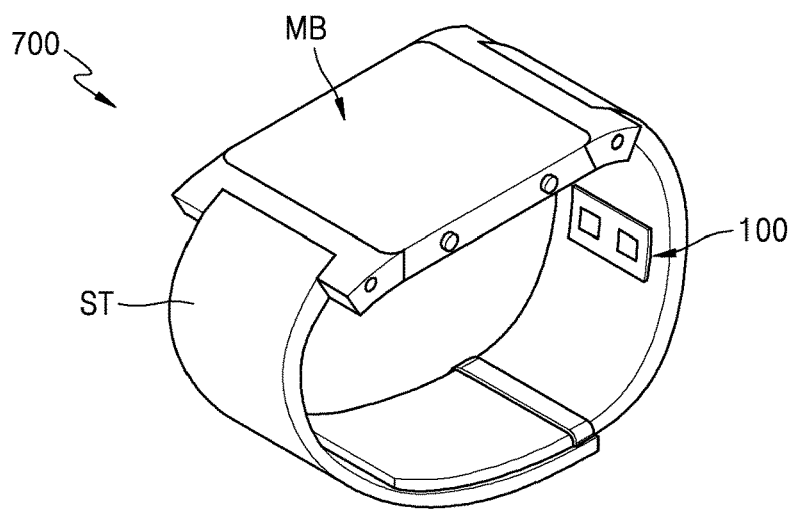
Figure 10:
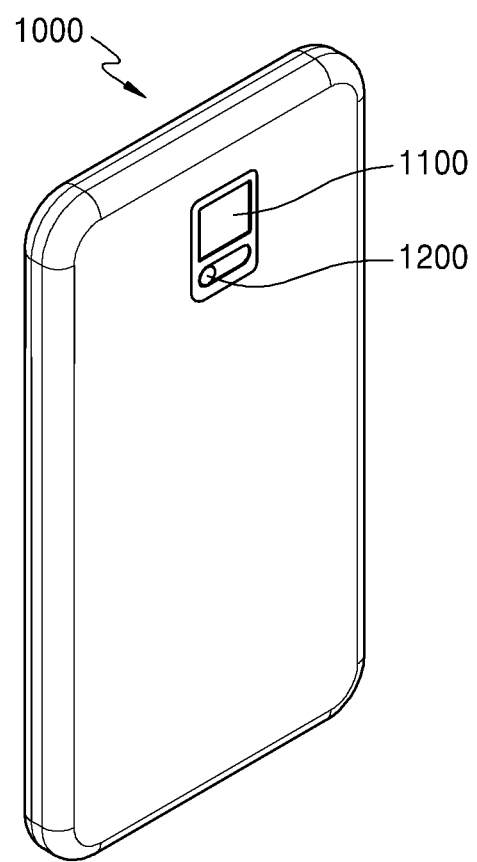

FIGS. 8 through 10 are perspective views of portable devices 500, 700, and 1000, each including the blood pressure measuring apparatus 10 according to exemplary embodiments. FIG. 8 illustrates an example of the wrist watch type device 500 in which the sensor 100 is installed in the back of a main body MB, light is radiated to the back of an arm or a hand, a change in a blood stream is detected as a signal change of light, and no sensor is installed in a strap ST. FIG. 9 illustrates an example of the wrist watch type device 700 in which the sensor 100 is provided in the strap ST, light is radiated to a radial artery, and a change in a blood stream flowing in the radial artery is detected as a signal change of light. FIG. 10 illustrates an example of the smart phone 1000 in which an image sensor 1100, i.e., a CIS, and a light source 1200 are provided on the back of the smart phone 1000, and are used to detect a change in a blood stream flowing in a finger as a signal change of light. The image sensor 1100 and the light source 1200 provided on the back of the smart phone 1000 may be respectively used as the light emitting device 111 of the light emitter 110 and the light receiving device 151 of the light receiver 150 of the blood pressure measuring apparatus 10.

Figure 11:
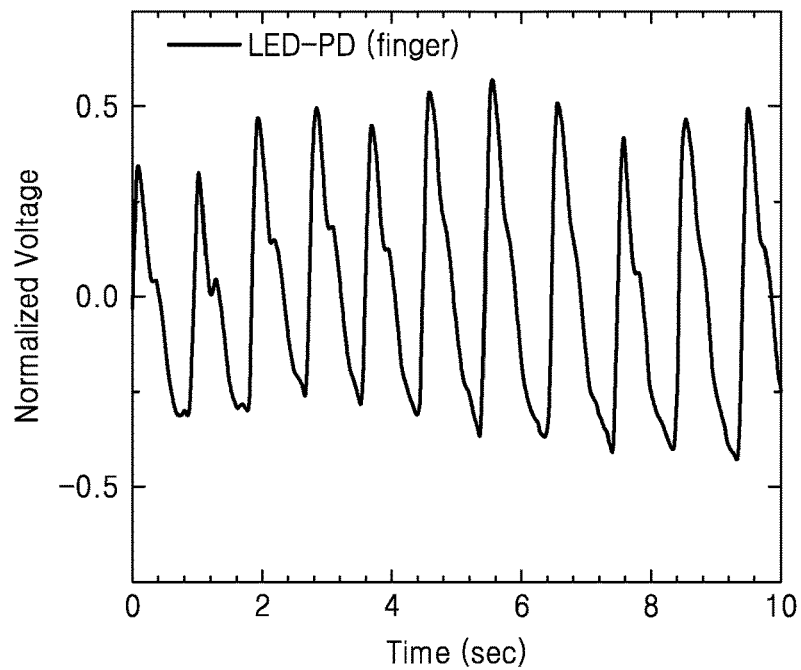
FIG. 11 is a graph of a waveform when a sensor of a light emitting diode-photo diode (LED-PD) combination radiates light toward a finger and detects a change in a blood stream as a signal change of light according to an exemplary embodiment.
Figure 12:
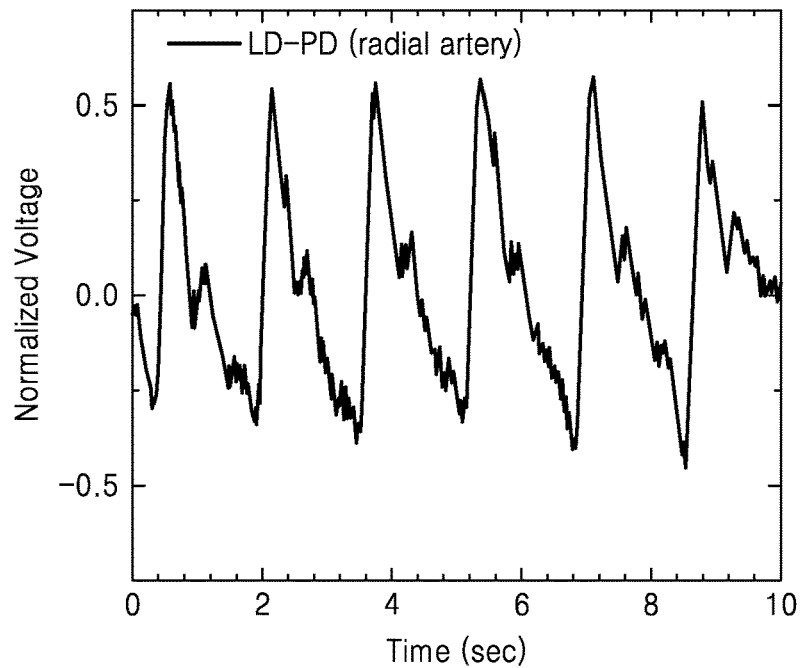
FIGS. 12 through 14 are graphs of waveforms when a sensor of an LED-PD combination radiates light toward a radial artery, to above a wrist, and to a finger, respectively, and detects a change in a blood stream as a signal change of light according to exemplary embodiments.
Figure 13:
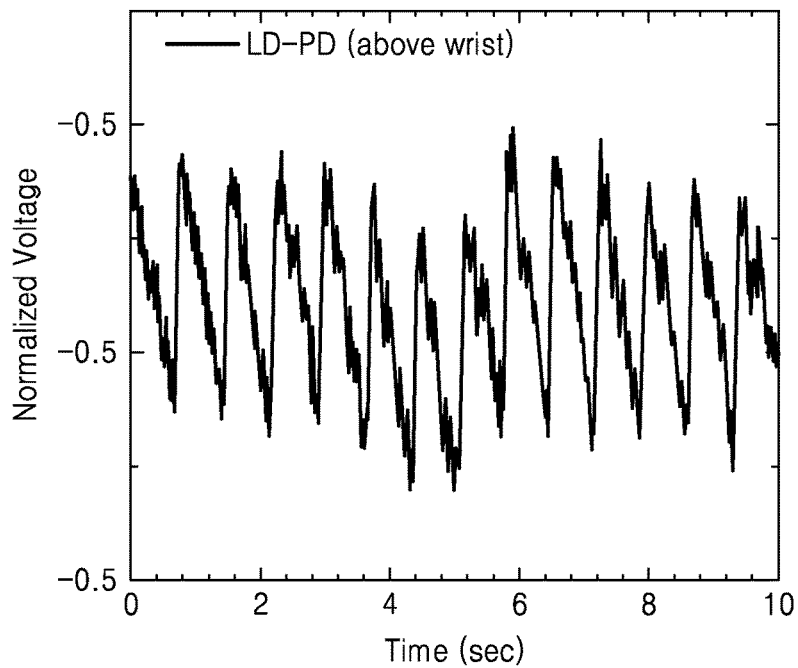
Figure 14:
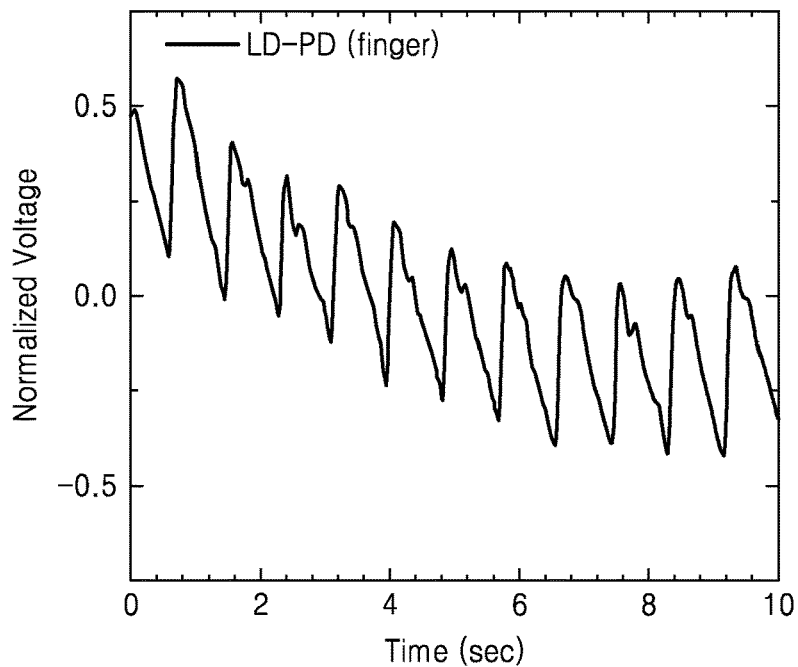

FIG. 11 is a graph of a waveform when a sensor of a light emitting diode-photo diode (LED-PD) combination radiates light to a finger and detects a change in a blood stream as a signal change of light according to an exemplary embodiment. FIGS. 12 through 14 are graphs of waveforms when a sensor of a laser diode-photo diode (LD-PD) combination radiates light to a radial artery, to above a wrist, and to a finger, respectively, and detects a change in a blood stream as a signal change of light according to exemplary embodiments.

As seen from a comparison of FIG. 11 and FIGS. 12 through 14, when not only a LED but also a laser diode is used as the light emitting device 111 of the light emitter 110, a signal indicating the change in the blood stream may be measured. When the laser diode is used, even though the sensor 100 is placed above the wrist, the signal indicating the change in the blood stream may also be measured. When the light emitting device 111 suitable for the light emitter 110 is selected, the signal indicating the change in the blood stream may be measured not only at the finger or the radial artery but also above the wrist, and the signal may be analyzed to estimate a value of a HR and calculate an estimation value of a blood pressure value. In addition, when the light emitting device 111 suitable for the light emitter 110 is selected, the signal indicating the change in the blood stream may be measured without a limitation to a position of a body part, and the signal may be analyzed to calculate estimation values of the blood pressure values and the HR value.

The blood pressure measuring apparatus 10 according to the exemplary embodiment described above may use one of a linear regression analysis, a multiple regression analysis, a non-linear regression analysis as a blood pressure estimation algorithm to calculate the blood pressure estimation value by using a plurality of pieces of feature point data extracted with respect to each cycle waveform of a bio signal. As the blood pressure estimation algorithm, one of machine learning algorithms, for example, an artificial neural network (ANN) algorithm, a K-nearest neighbor (KNN) algorithm, a Bayesian network algorithm, a support vector machine (SVM) algorithm, and a recurrent neural network algorithm may be used. In this regard, the machine learning algorithm may perform prediction based on an already determined attribute through training data, for example, may predict a blood pressure by training a pulse waveform.

For example, the ANN algorithm is used to perform calculation with already learned data. The learned data may be stored in the memory 400 in a hidden layer matrix, the stored hidden layer matrix and newly measured data may be combined during an actual measurement, and a desired blood pressure estimation value may be calculated.

Although the blood pressure measuring apparatus 10 may not use the body information interface 310 according to circumstances, a learned matrix may be used as data collected from a population for each body feature rather than data collected from a randomly extracted population to more accurately calculate the blood pressure estimation value. Estimated data may be output on the display 330. The data transmitter 350 may transmit the blood pressure values and the HR value to a smart phone or a computer by using a communication protocol such as Bluetooth. The data transmitter 350 may be used to connect devices or connect a device to a clinic to allow the clinic to provide various services.

Figure 15A:
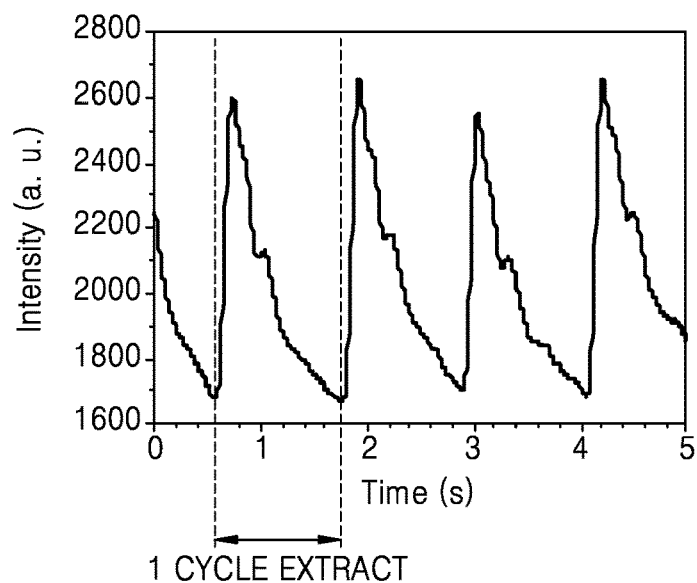
FIG. 15A is a graph of a measured pulse waveform according to an exemplary embodiment.
Figure 15B:
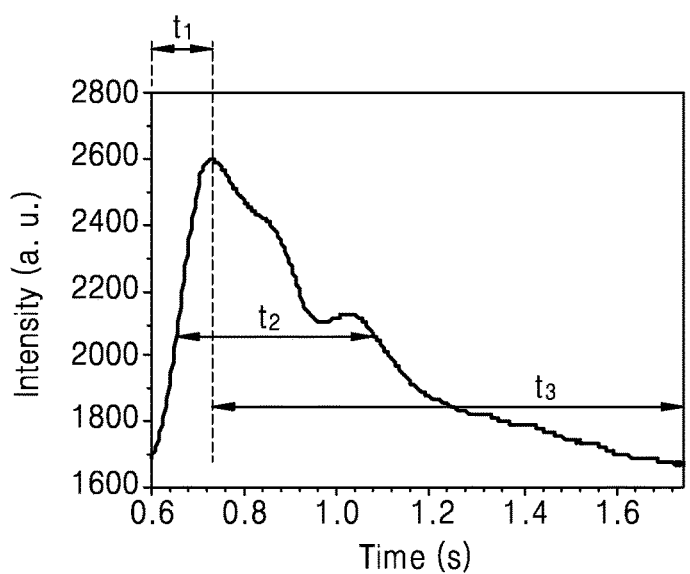
FIG. 15B is a graph of parameters that may be extracted from one cycle of the waveform of FIG. 15A.

FIG. 15A is a graph of a measured pulse waveform according to an exemplary embodiment, and FIG. 15B is a graph of parameters that may be extracted from one cycle of the waveform of FIG. 15A.

Referring to FIGS. 15A and 15B, a waveform corresponding to one cycle of a pulse waveform is extracted, and parameters, for example, t1, t2, t3, etc., that may be estimated to be related to a blood pressure are extracted. The waveform of FIGS. 15A and 15B may correspond to, for example, a PPG pulse.

Referring to FIG. 15B, t1 denotes a systolic upstroke time, t2 denotes a diastolic time, and t3 denotes a width of a waveform in a predetermined location. t3 data may be obtained in a plurality of locations. Data of a width during a systolic time and a width during the diastolic time in the predetermined location or in the plurality of locations may be obtained as the t3 data.

As described above, the parameters relating to the blood pressure may be extracted from the pulse waveform, and may be used to estimate a blood pressure value.

Figure 16:
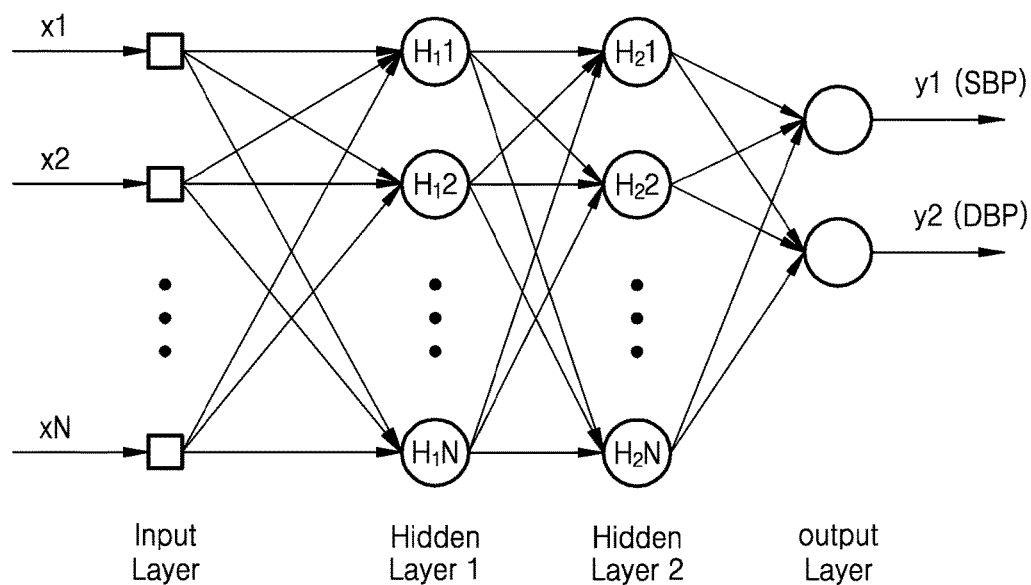
FIG. 16 is a diagram illustrating an artificial neural network (ANN) algorithm according to an exemplary embodiment.

FIG. 16 is a diagram illustrating an ANN algorithm according to an exemplary embodiment.

Referring to FIG. 16, a plurality of hidden layers, for example, two layers, which are hidden between a maximum point and a minimum point of blood pressure values corresponding to values of feature points of a bio signal obtained as described above, may be set in an input layer of the ANN algorithm. The values of the feature points and blood pressure values may be used to form a network such as a neural network. In such structure, a pattern may be learned by repetitively using various pieces of data extracted from the population, and the blood pressure values for a new input may be estimated by calling a learned hidden layer matrix. FIG. 16 illustrates the example of the ANN algorithm configured to form a hidden layer matrix structure through machine learning to output y1 (SBP) and y2 (DBP) in an output layer by corresponding extracted various pieces of feature point data x1, x2, . . . , xN that are input in an input layer to hidden layers, for example, Hidden Layer 1 and Hidden Layer 2. When the ANN algorithm is configured as shown in FIG. 16, output data may be estimated by using a learned hidden layer matrix with respect to arbitrarily input data.

Figure 17:
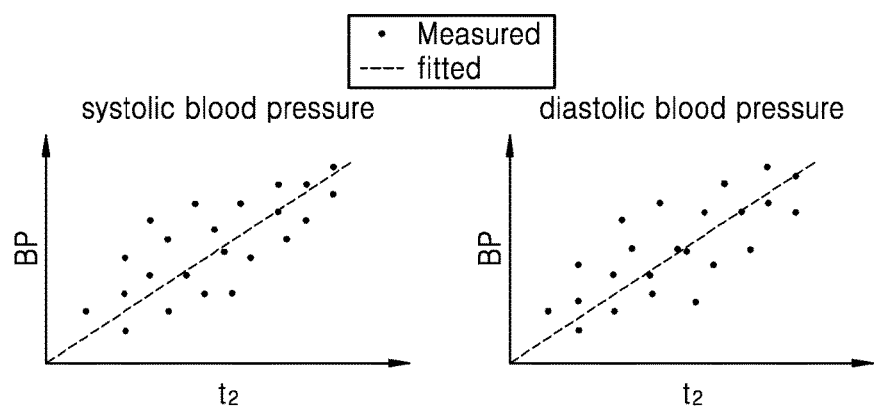
FIG. 17 is a diagram illustrating a linear regression analysis algorithm according to an exemplary embodiment.

FIG. 17 is a diagram illustrating a linear regression analysis algorithm according to an exemplary embodiment.

When the linear regression analysis algorithm is applied as shown in FIG. 17, coefficient values of a linear relation equation between extracted feature point data and blood pressure values are calculated by analyzing the linear relation equation using a plurality of pieces of data. The calculated coefficient values may be used to calculate a linear relation equation, and a blood pressure value with respect to a new input feature may be estimated by using the linear relation equation. FIG. 17 illustrates a result of estimating SBP and DBP values with a diastolic time t2 of a pulse waveform as a horizontal axis. The extracted parameters may be used to calculate the linear relation equation between the parameters and the blood pressure. For example, a linear relation equation of the SBP may be obtained as Sys BP=a1t2+b1, and a linear relation equation of the DBP may be obtained as Dia BP=a2t2+b2. In this regard, a1, b1, a2, and b2 are calculated fitting parameters. As another example, a linear relation equation of the blood pressure may be obtained as BP=a1t1+a2t2+a3t3 . . . +C. The linear relation equation may be used to estimate a blood pressure value with respect to a new input.

A case where the ANN algorithm is applied as a blood pressure estimation algorithm applied to the blood pressure measuring apparatus 10 according to an exemplary embodiment will be described below.

When the ANN algorithm is applied as the blood pressure estimation algorithm, a data learning process is firstly performed. During the data learning process, a hidden layer matrix is calculated by applying feature points extracted with respect to a bio signal to the ANN algorithm and then is stored in the memory 400. Thereafter, when a blood pressure is actually measured, the feature points with respect to a bio signal are extracted, and blood pressure values, for example, a SBP, a DBP, and a HR, are calculated by using a combination of data of the feature points and the hidden layer matrix stored in the memory 400.

Figure 18:
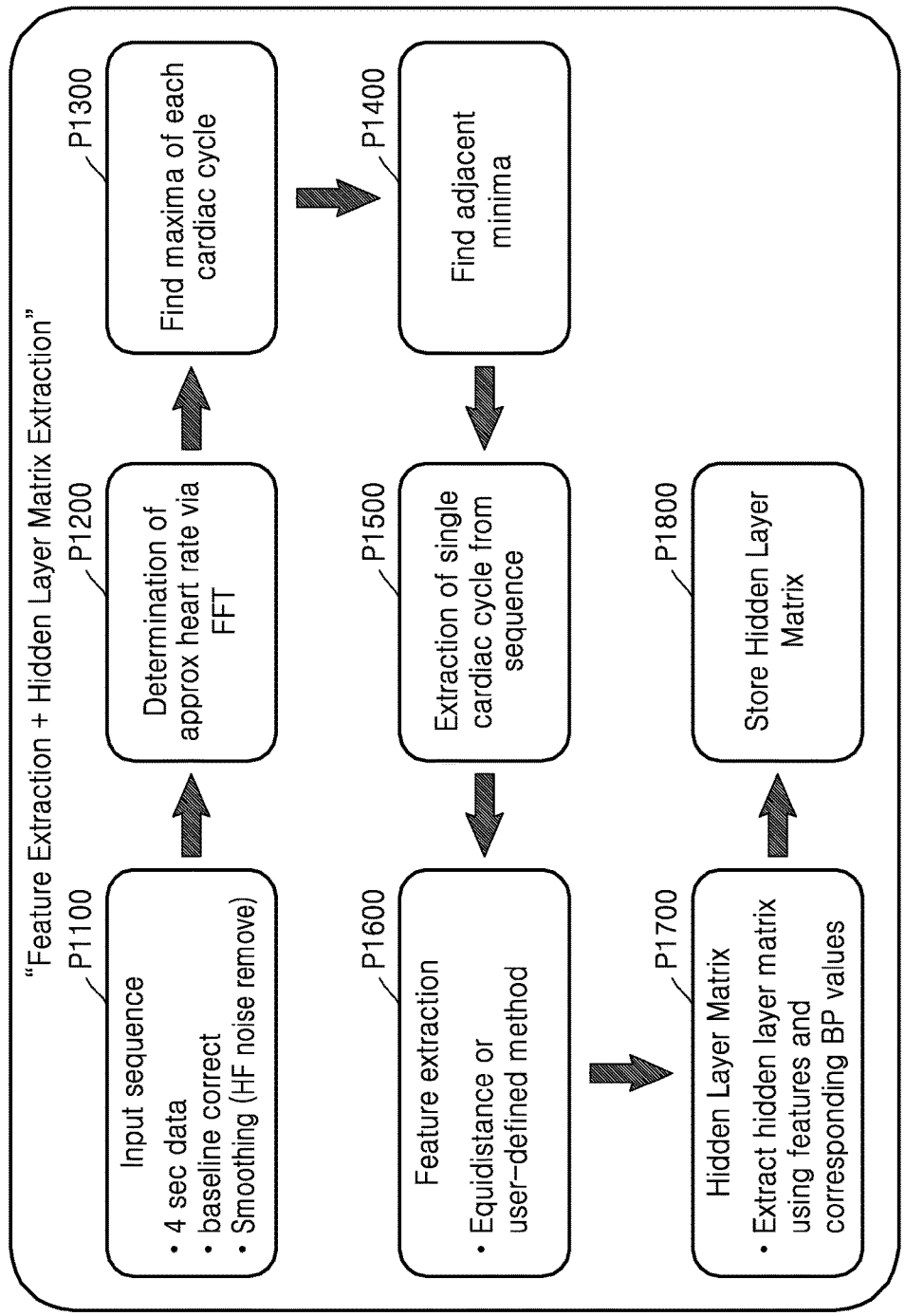
FIG. 18 is a diagram illustrating a data learning process in an ANN algorithm used by a blood pressure measuring apparatus according to an exemplary embodiment.

FIG. 18 is a diagram illustrating a data learning process of an ANN algorithm used by the blood pressure measuring apparatus 10 according to an exemplary embodiment.

Referring to FIG. 18, light is radiated to an examined body part, and a bio signal sequence obtained by detecting a signal change in light due to the examined body part is input (operation P1100). An input bio signal is data obtained for a predetermined period of time, for example, for 4 seconds, and from which a baseline is corrected and high frequency HF noise is removed through processing the bio signal by using, for example, a smoothing function or a filter. An approximate HR estimation value may be determined by performing fast Fourier transform (FFT) on the bio signal sequence (operation P1200), and a maximum point of each cardiac cycle waveform and a minimum point adjacent to the maximum point are analyzed (operations P1300 and P1400). Thereafter, one cardiac cycle waveform is extracted from the bio signal sequence (operation P1500), and a plurality of feature points for the cardiac cycle waveform are extracted at equidistant intervals or by using a user-defined method (operation S1600). The extracted feature points are used to extract a hidden layer matrix and blood pressure values corresponding to the hidden layer matrix (operation S1700), and a result of a learned hidden layer matrix is stored in the memory 400 (operation P1800).

Figure 19:
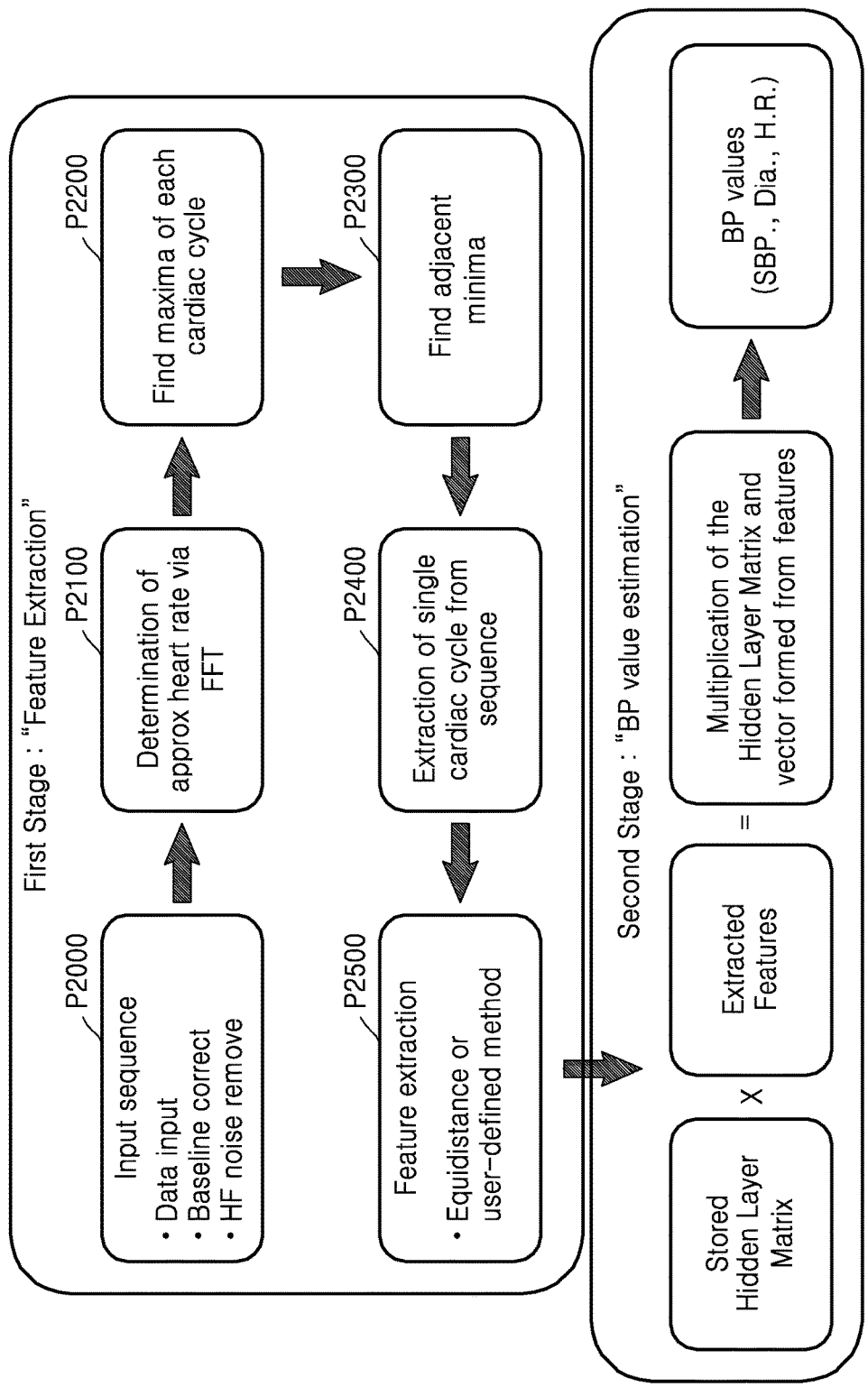
FIG. 19 is a diagram illustrating a process of calculating blood pressure values by using a stored hidden layer matrix after extracting feature points via an ANN algorithm according to an exemplary embodiment.

FIG. 19 is a diagram illustrating a process of calculating blood pressure values by using a stored hidden layer matrix after extracting feature points via an ANN algorithm according to an exemplary embodiment.

Referring to FIG. 19, the process of estimating and calculating blood pressure (BP) values may be largely divided into a process (first operation) of extracting feature points from a bio signal and a process (second operation) of calculating the blood pressure values as a product between data of the extracted feature points and a stored hidden layer matrix obtained through a data learning process, for example, of the ANN algorithm.

To extract the data of feature points from the bio signal, light is radiated towards an examined body part, and a bio signal sequence obtained by detecting a signal change in light due to the examined body part is input (operation P2000). An input bio signal is data obtained for a predetermined period of time, for example, for 4 seconds, and from which a baseline is corrected and high frequency HF noise is removed by processing the bio signal using, for example, a smoothing function or a filter. An approximate HR estimation value is determined by performing FFT on the bio signal sequence (operation P2100), and a maximum point of each cardiac cycle waveform and a minimum point adjacent to the maximum point is analyzed (operations P2200 and P2300). Thereafter, one cardiac cycle waveform is extracted from the bio signal sequence (operation P2400), and a plurality of feature points are extracted for the cardiac cycle waveform at equidistant intervals or by using a user-defined method, for example, extracting the plurality of feature points at non-equidistant intervals (operation S2500).

The blood pressure values may be calculated by using data of the extracted feature points and a hidden layer matrix stored in the memory 400. The blood pressure values may be obtained from, for example, as a product between the hidden layer matrix and a vector formed as the data of the feature points. In this regard, the blood pressure values obtained as a result of calculation may include a SBP, a DBP, and a HR. The measured blood pressure and the HR may be displayed on the display 330 and/or may be output to an external device.

Figure 20A:
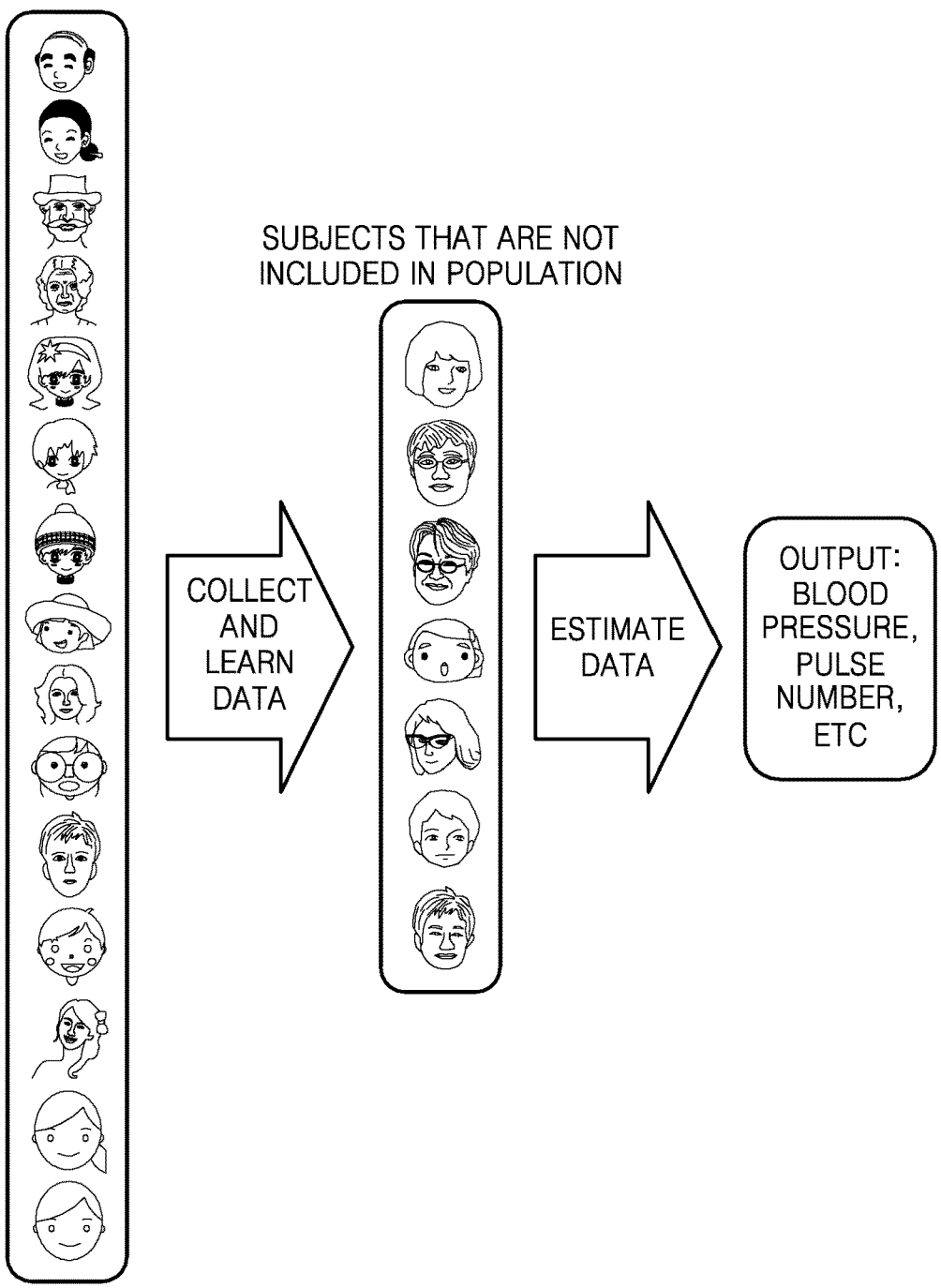
FIGS. 20A through 20C are diagram illustrating a process of collecting and predicting data that may be used during the data learning process of FIG. 18 according to exemplary embodiments.
Figure 20B:
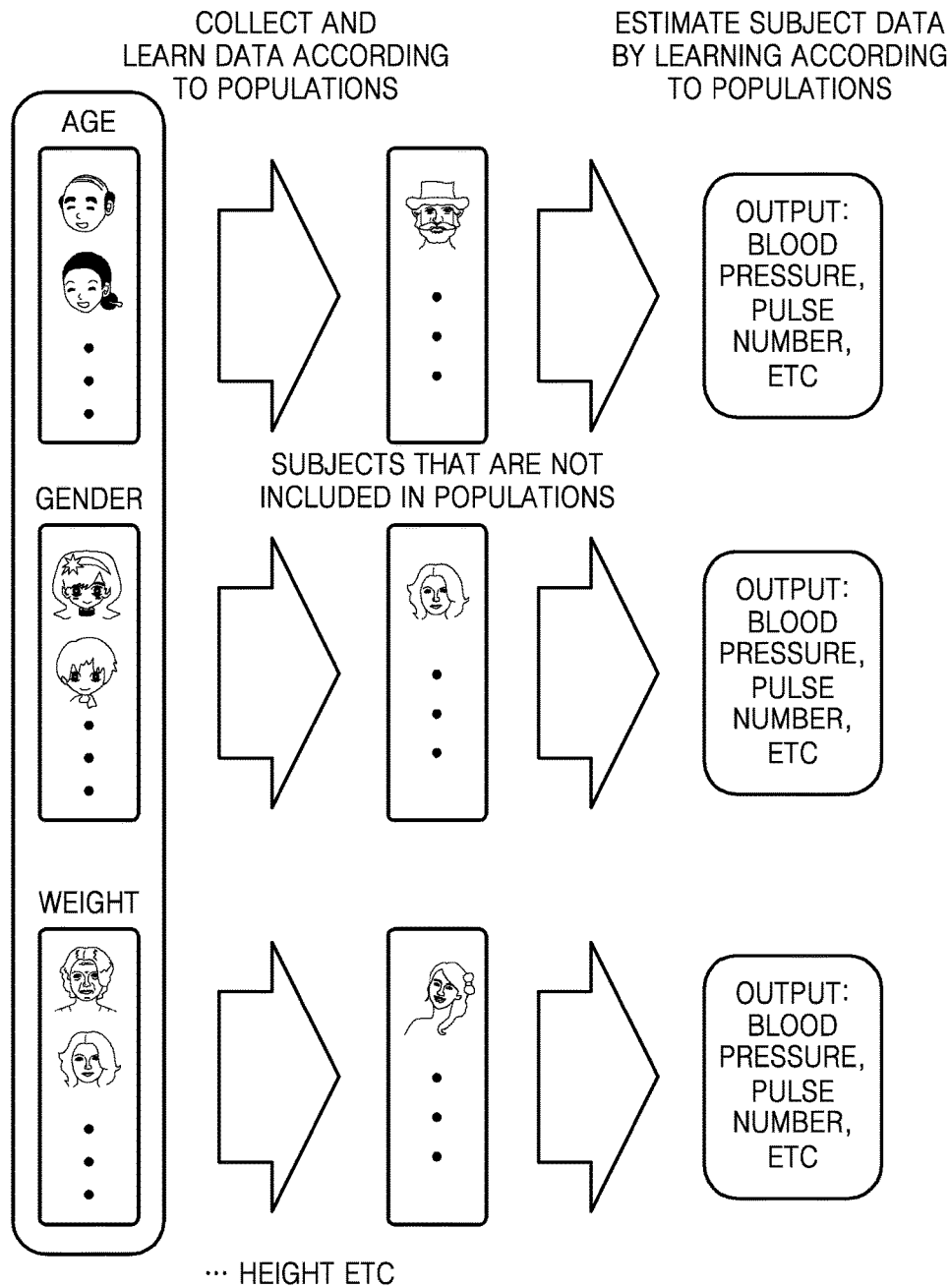
Figure 20C:
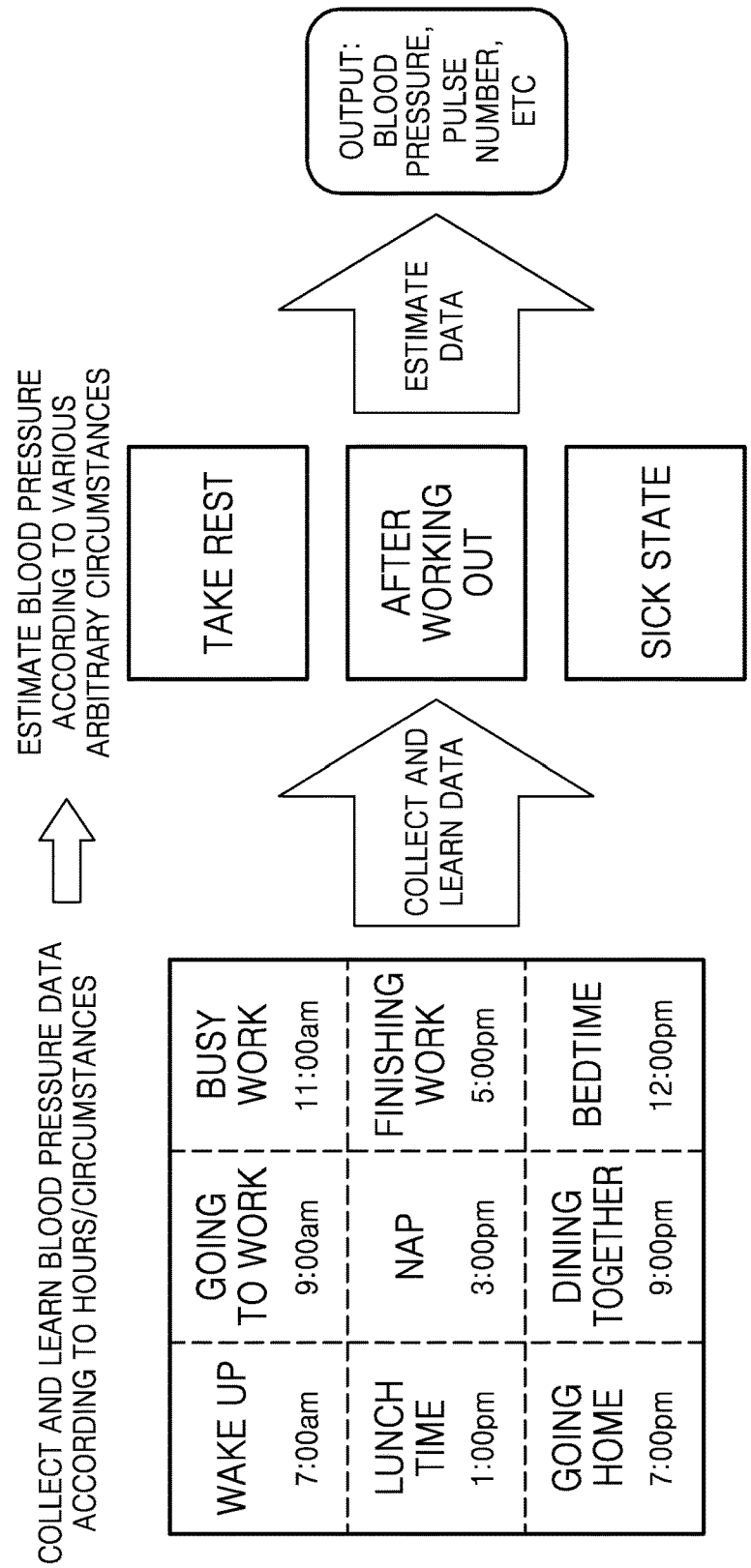

FIGS. 20A through 20C are diagrams illustrating a process of collecting and predicting data that may be used during a data learning process of FIG. 18 according to exemplary embodiments.

For example, as shown in FIG. 20A, a hidden layer matrix may be obtained by collecting and learning data by utilizing a randomly extracted population, and blood pressure values of a subject that is not included in the population may be estimated. As another example, as shown in FIG. 20B, to more accurately estimate blood pressure values, a hidden layer matrix may be obtained by classifying populations according to body features, and collecting and learning data according to the classified populations. The blood pressure values may be estimated by using data according to the classified populations corresponding to body features of subjects that are not included in these populations. As another example, as shown in FIG. 20C, a hidden layer matrix may be obtained a plurality of number of times by collecting and learning data according to individuals according to circumstances when individuals take a rest, work out, or are sick during 24 hours of a day. The hidden layer matrix may be used to estimate the blood pressure values according to individuals.

As described with reference to FIG. 7, when a baseline of the collected data by using the blood pressure estimation algorithm above moves, the baseline is corrected by using a primary, secondary, or tertiary function, and when high frequency HF noise is present, the data is processed using, for example, a smoothing function, to remove the noise. Thereafter, one cycle is subdivided to determine minimum and maximum values for each cycle and extract feature points for each cycle. In this regard, equidistant intervals or a user-defined method is used to extract the feature points. Data of the extracted feature points may be applied to the blood pressure estimation algorithm to calculate and estimate the blood pressure values and a HR value.

As described above, according to the above exemplary embodiments, the blood pressure may be measured based on an optical signal, and thus the apparatus for and method of measuring the blood pressure may be implemented via a cuffless structure. The blood pressure values may be estimated and calculated by using feature point data of a bio signal in a blood pressure estimation algorithm, and thus, the blood pressure may be continuously monitored for a long time and the apparatus may be implemented in a wearable device or portable device.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus configured to measure blood pressure, the apparatus comprising:
    a sensor configured to radiate light to a body part, and detect a light signal that is changed due to the body part to which the light is radiated;
    a signal processor configured to determine a bio signal, based on the light signal; and
    a central processing unit configured to:
        correct the bio signal;
        extract feature points from the bio signal that is corrected;
        input the feature points into an artificial neural network algorithm to learn a hidden layer matrix of the artificial neural network algorithm;
        estimate a plurality of blood pressures as a product between the hidden layer matrix and a vector that is formed from the feature points;
        extract one cycle of the bio signal that is corrected;
        extract a systolic upstroke time interval and a diastolic time interval from the one cycle;
        determine a linear relation equation of a blood pressure, from the plurality of blood pressures over the systolic upstroke time interval and the diastolic time interval; and
        determine the blood pressure, based on the linear relation equation.

2. The apparatus of claim 1, wherein the signal processor is further configured to:
    extract a cycle of the light signal; and
    sample data from the cycle of the light signal at equidistant time intervals or based on a user input.

3. The apparatus of claim 1, wherein the signal processor is further configured to:
    compare power spectrums within a frequency range of bio signals that are determined based on channels; and
    select a channel having a maximum power spectrum from the channels.

4. The apparatus of claim 3, wherein, the signal processor is further configured to, in response to the signal processor selecting the channel having the maximum power spectrum or using a single channel, select a part of a bio signal that corresponds to the channel that is selected or the single channel, in which a power spectrum value within the frequency range is greater than a value, as a valid part of the bio signal.

5. The apparatus of claim 1, further comprising a display configured to display the blood pressure.

6. The apparatus of claim 1, further comprising a memory configured to store a blood pressure estimation algorithm and information of the bio signal.

7. The apparatus of claim 1, wherein the sensor comprises a light emitter configured to radiate the light to the body part, and a light receiver configured to detect the light signal that is changed due to the body part,
the light receiver comprises a photodiode or an image sensor, and
the light emitter comprises a laser diode or a light emitting diode.

8. The apparatus of claim 1, wherein the sensor comprises a light emitter configured to radiate the light to the body part, and a light receiver configured to detect the light signal that is changed due to the body part,
the light emitter comprises a laser diode, and
the central processing unit is further configured to determine the blood pressure, based on the bio signal in response to the sensor being spaced apart from a skin of an examinee.

9. The apparatus of claim 1, wherein the bio signal is periodically obtained at predetermined time intervals.

10. The apparatus of claim 1, wherein the central processing unit is further configured to correct the blood pressure, based on another blood pressure that is determined by another device.

11. The apparatus of claim 1, further comprising a body information interface configured to receive body information of at least one among an age, a gender, a weight, and a height of an examinee,
wherein the central processing unit is further configured to determine the blood pressure, based on the bio signal and the body information.

12. The apparatus of claim 1, wherein the apparatus is portable, and is implemented in one among a wrist watch, a mobile smart phone, a tablet computer, an earphone, a headset, and glasses.

13. The apparatus of claim 1, wherein the apparatus is implemented in a wrist watch, and the sensor is positioned on a back of a main body or a strap of the wrist watch.

14. A method of measuring blood pressure, the method comprising:
radiating light to a body part;
detecting a light signal that is changed due to the body part to which the light is radiated;
determining a bio signal, based on the light signal;
correcting the bio signal;
extracting feature points from the bio signal that is corrected;
inputting the feature points into an artificial neural network algorithm to learn a hidden layer matrix of the artificial neural network algorithm;
estimating a plurality of blood pressures as a product between the hidden layer matrix and a vector that is formed from the feature points;
extracting one cycle of the bio signal that is corrected;
extracting a systolic upstroke time interval and a diastolic time interval from the one cycle;
determining a linear relation equation of the blood pressure, from the plurality of blood pressures over the systolic upstroke time interval and a diastolic time interval; and
determining the blood pressure, based on the linear relation equation.

15. The method of claim 14, wherein the extracting comprises:
determining a maximum point of the bio signal that is corrected and a minimum point adjacent to the maximum point; and
extracting the feature points from the bio signal that is corrected at equidistant time intervals or based on a user input.

16. The method of claim 14, wherein the correcting comprises:
correcting a baseline of a sequence of the bio signal; and
removing high frequency noise from the sequence that is corrected.

* * * * *